US008801621B2

(12) United States Patent
Kitajima et al.

(10) Patent No.: US 8,801,621 B2
(45) Date of Patent: Aug. 12, 2014

(54) METHOD, SYSTEM AND PROGRAM PRODUCT FOR ANALYZING PULSE WAVE DATA

(75) Inventors: Kazumi Kitajima, Higashiosaka (JP); Yoshiroh Nagai, Nishinomiya (JP)

(73) Assignee: Konica Minolta Sensing, Inc., Osaka (JP)

( * ) Notice: Subject to any disclaimer, the term of this patent is extended or adjusted under 35 U.S.C. 154(b) by 1706 days.

(21) Appl. No.: 12/079,469

(22) Filed: Mar. 27, 2008

(65) Prior Publication Data

US 2008/0249423 A1 Oct. 9, 2008

(30) Foreign Application Priority Data

Apr. 5, 2007 (JP) ................................ 2007-099799

(51) Int. Cl.
*A61B 5/02* (2006.01)
*A61B 5/00* (2006.01)
*A61B 5/021* (2006.01)
*A61B 5/024* (2006.01)
*A61B 5/0285* (2006.01)

(52) U.S. Cl.
CPC ............ *A61B 5/02416* (2013.01); *A61B 5/6838* (2013.01); *A61B 5/7264* (2013.01); *A61B 5/02116* (2013.01); *A61B 5/7203* (2013.01); *A61B 5/6826* (2013.01); *A61B 5/0285* (2013.01)
USPC ............................ 600/500; 600/502; 600/504

(58) Field of Classification Search
CPC ...... A61B 5/024; A61B 5/02416; A61B 5/02; A61B 5/02007; A61B 5/0205; A61B 5/021; A61B 5/02208; A61B 5/02438; A61B 5/0285; A61B 5/029; A61M 2230/04; A61M 2230/005
See application file for complete search history.

(56) References Cited

U.S. PATENT DOCUMENTS 6,095,984 A 8/2000 Amano et al.
6,519,486 B1 * 2/2003 Edgar et al. ................... 600/336

FOREIGN PATENT DOCUMENTS

| JP | 08-229013 | 9/1996 |
| JP | 2001-070265 | 3/2001 |
| JP | 3635663 B2 | 4/2005 |
| WO | WO 97/38626 | 10/1997 |

* cited by examiner

*Primary Examiner* — Benjamin P Blumel
(74) *Attorney, Agent, or Firm* — Brinks Gilson & Lione

(57) ABSTRACT

A pulse wave data analyzing method includes successively detecting bottom and top peak values of pulse wave data along a time axis, calculating successive bottom-to-top amplitude values along the time axis, and comparing first and second peak-to-peak amplitude values occurring in succession along the time axis. If the ratio of the second peak-to-peak amplitude value to the first peak-to-peak amplitude value is smaller than a preset threshold, the bottom and top peak values related to the second peak-to-peak amplitude value are classified as temporarily erased data. The second peak-to-peak amplitude value is compared with a third peak-to-peak amplitude value occurring immediately thereafter and, if the ratio between the second and third peak-to-peak amplitude values is larger than the threshold, the temporarily erased data is restored. If the ratio between the second and third peak-to-peak amplitude values is not larger than the threshold, the temporarily erased data is completely erased.

7 Claims, 19 Drawing Sheets

METHOD, SYSTEM AND PROGRAM PRODUCT FOR ANALYZING PULSE WAVE DATA

This application is based on Japanese Patent Application No. 2007-099799 filed on Apr. 5, 2007, the contents of which are hereby incorporated by reference.

BACKGROUND OF THE INVENTION

1. Field of the Invention

The present invention relates to a method, a system and a program for analyzing pulse wave data used especially for extracting information concerning RR intervals, for example, from an electrocardiogram.

2. Description of the Related Art

Measurement of RR intervals on an electrocardiogram (ECG) taken from a subject is a widely used method of diagnosing cardiac arrhythmias. As shown in FIG. 19, the RR interval is a period of time between peaks of two successive R waves which are the most prominent among P, Q, R, S and T waves occurring in one heartbeat cycle on an ECG tracing. Successive readings of RR intervals, when arranged time-sequentially, make it possible to recognize heartbeat variations which are commonly used in clinical applications as an evaluation index for diagnosing biological control functions performed by an autonomic nervous system in human body activities.

Electrocardiographic measurement is performed by using a Holter monitor, for instance, which is provided with electrodes for sensing electrical potentials produced by muscular activity of the heart. The Holter monitor often used in a medical institution is a wearable device including a plurality of (e.g., five) electrodes attached to the chest of a subject and a data recorder worn by the subject at the waste or over the shoulder for recording data received from the electrodes. The Holter monitor is typically worn for 24 hours and the subject is encouraged to continue his or her daily activities. Upon completion of Holter monitoring, the data stored in the data recorder is transferred to an analyzer which performs an analysis of recorded heartbeat patterns to determine RR intervals. One chronic problem of this conventional Holter monitoring approach is that the subject is forced to endure conditions of substantial stress as the subject must continue daily activities while wearing the data recorder and the electrodes.

An alternative measurement method intended to overcome this problem is currently under study. This method is to extract information concerning RR intervals from pulse wave data without using ECGs, where a pulse wave is representative of a vasomotor response observed on the body surface as a pattern of volumetric changes of any artery caused by an inflow of blood thereinto. The pulse wave is closely related to (or synchronized with) pumping motion of the heart and, thus, it is possible to obtain information indirectly representing the RR interval by measuring movements of peripheral blood vessels.

As an example, Japanese Unexamined Patent Publication No. 1997-229013 describes a pulse wave RR interval measuring apparatus comprising a pulse wave sensor which continuously detects pulse waves of a subject and calculation means which determines peak values and peak points by analyzing pulse wave data detected by the pulse wave sensor and calculates the RR interval. Also, Japanese Patent No. 3635663 disposes an arrhythmia sensing apparatus which is configured to perform frequency analysis of a pulse waveform detected by a pulse waveform sensing device, exactly detect pulse wave components by filtering out body movement components from the pulse waveform and discover the presence of any cardiac arrhythmia using results of the pulse waveform frequency analysis. In addition, Japanese Unexamined Patent Publication No. 2001-70265 proposes a method of pulse wave analysis for determining the RR interval by calculating a first derivative of a plethysmogram (pulse wave) obtained by a pulse wave sensor to produce a velocity plethysmogram and detecting peaks of the velocity plethysmogram.

Peaks occurring in pulse wave data are however not so prominent as R waves observed on an ECG and, in addition, the pulse wave data contains small notches and reflected wave components which act as noise in a process of peak detection. These notches and reflected wave components are relatively small peaks (top peaks) and valleys (bottom peaks) in a pulse waveform. For the sake of simplification of the following discussion, the notches and reflected wave components in the pulse wave data are hereinafter referred to simply as "notches." Due to the presence of these unwanted notches, it is not conventionally so easy to automatically detect peaks corresponding to the R waves in a raw pulse waveform. Neither the aforementioned Unexamined Patent Publication No. 1997-229013 nor U.S. Pat. No. 3,635,663 makes any mention of a method of exactly extracting peaks from the pulse wave data. Although the pulse wave analysis method proposed in Japanese Unexamined Patent Publication No. 2001-70265 is supposed to be able to remove unwanted notches to a certain degree, true peaks of the pulse wave might be judged as noise if the occurrence of such peaks is not predictable like those caused by arrhythmia. This is because an approach employed in the pulse wave analysis method of the Publication is to remove notches by using a threshold defined based on a mean value of peak intervals.

SUMMARY OF THE INVENTION

It is an object of the present invention to provide a method, a system and a program for analyzing pulse wave data which can solve the aforementioned problems in the prior art.

It is another object of the present invention to provide a method, a system and a program for analyzing pulse wave data which make it possible to exactly detect peaks (top peaks) and valleys (bottom peaks) of the pulse wave data by removing notch portions contained therein and acquire biometric information, such as intervals of top peaks (or bottom peaks) of the pulse wave data which are highly correlated with RR intervals observed on an ECG, even when a subject is suffering from cardiac arrhythmia or like abnormalities.

According to an aspect of the invention, biometric information is extracted from pulse wave data taken from a living body by: successively detecting bottom peak values and top peak values of the pulse wave data obtained by continuously measuring a pulse wave for a specific period of time along a time axis, combining two adjacent bottom and top peak values detected in succession along the time axis in pairs, calculating a bottom-to-top amplitude value which is a difference between the bottom and top peak values of each successive pair along the time axis, comparing a first peak-to-peak amplitude value and a second peak-to-peak amplitude value which correspond to two successive bottom-to-top amplitude values occurring in succession along the time axis, classifying the bottom and top peak values related to the second peak-to-peak amplitude value as temporarily erased data if the ratio of the second peak-to-peak amplitude value to the first peak-to-peak amplitude value is smaller than a preset threshold, comparing the second peak-to-peak amplitude value with a third peak-to-peak amplitude value which occurs in succession to the second peak-to-peak amplitude value, restoring the temporarily erased bottom and top peak values related to the second peak-to-peak amplitude value as data to be used for pulse wave data analysis by canceling classification of the bottom and top peak values related to the second peak-to-peak amplitude value as the temporarily erased data if the ratio between the second and third peak-to-peak amplitude values is larger than the preset threshold, and completely erasing the temporarily erased bottom and top peak values related to the second peak-to-peak amplitude value by regarding the bottom and top peak values as noise if the ratio between the second and third peak-to-peak amplitude values is not larger than the preset threshold.

These and other objects, features and advantages of the invention will become more from the following detailed description when read along with the accompanying drawings.

DETAILED DESCRIPTION OF THE PREFERRED EMBODIMENT OF THE INVENTION

A preferred embodiment of the invention is now described in detail with reference to the accompanying drawings.

Figure 1:
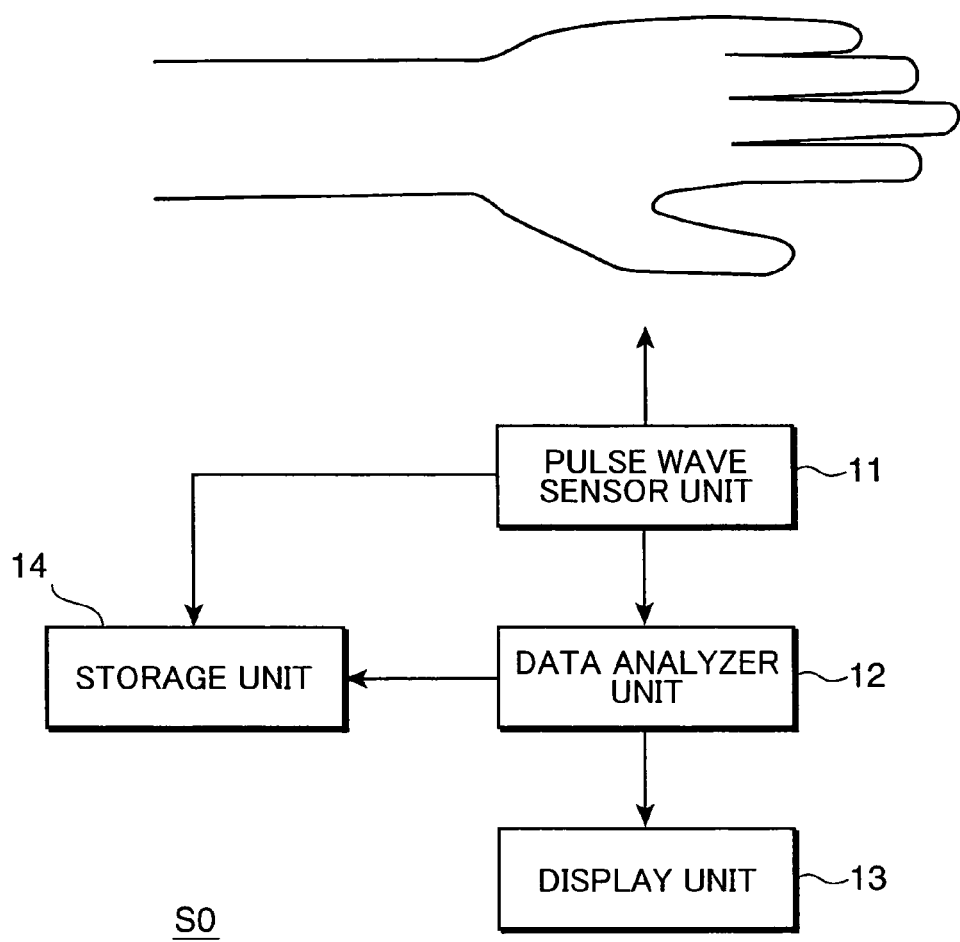
FIG. 1 is a block diagram generally showing the configuration of a pulse wave data analyzing system according to a preferred embodiment of the invention.

FIG. 1 is a block diagram generally showing the configuration of a pulse wave data analyzing system S0 according to the preferred embodiment having a capability to extract information concerning PP intervals which are substantially equivalent to RR intervals observed on an ECG from pulse wave data taken from a subject (living body). The pulse wave data analyzing system S0 comprises a pulse wave sensor unit 11, a data analyzer unit 12, a display unit 13 and a storage unit 14.

The pulse wave sensor unit 11 acquires the pulse wave data (data obtained by continuously measuring a pulse wave for a specific period of time) varying along a time axis. The pulse wave data is obtained by measuring information on the pulse wave taken from the subject at specified sampling intervals. Among various methods available for detecting the pulse wave, one of preferable methods would be to use a light absorption characteristic of hemoglobin in the blood, for example. This method is based on the fact that hemoglobin in the blood absorbs light. When light is projected on a living body part, part of the incident light is reflected while another part of the incident light is absorbed, wherein the amounts of reflected light and transmitted light vary with time because the amount of hemoglobin in blood vessels in the living body part under test varies in a wavy pattern due to blood flow pulsation caused by heartbeats.

It is possible to measure the pulse wave by monitoring the amount of light detected by a reflected light sensor or a transmitted light sensor mounted on a fingertip, for example, each of the sensors being provided with a combination of light-emitting and photosensitive elements. Known examples of the reflected light and transmitted light sensors are a photoplethysmographic device and a pulse oximeter capable of measuring blood oxygen saturation. It is also possible to acquire the pulse wave data by directly detecting pulse pressures caused by blood vessel pulsations by means of a pressure sensor.

The data analyzer unit 12 includes a read-only memory (ROM) storing various control programs, a random access memory (RAM) for temporarily storing data, a central processing unit (CPU) and a digital signal processor (DSP) which perform mathematical processing operation on the data according to the control programs read out from the ROM to analyze the pulse wave data acquired by the pulse wave sensor unit 11. As will be discussed later in detail, the data analyzer unit 12 temporarily erases some part of the pulse wave data when the data satisfies particular conditions and, then, restores or completely erases that part of the data to thereby perform noise filtering operation for removing notch noise components contained in the pulse wave data. Subsequently, the data analyzer unit 12 performs mathematical operation for determining intervals of top peaks (or bottom peaks) appearing on a pulse waveform based on the pulse wave data which has passed through the noise filtering operation.

The display unit 13 includes such a display device as a liquid crystal display (LCD), a seven-segment light-emitting diode (LED) display, an organic photoluminescence display, a plasma display or a cathode ray tube (CRT) for presenting data processed by the data analyzer unit 12. The display unit 13 shows various kinds of measurement information, such as results of analysis of the pulse wave data which may contain text information, image information, illumination/extinction of one or more points of light, or information expressed in whatever form necessary.

The storage unit 14 which may employ a RAM or an erasable programmable read-only memory (EPROM), for instance, is for temporarily storing such data as the pulse wave data obtained by the pulse wave sensor unit 11 and the results of analysis of the pulse wave data obtained by the data analyzer unit 12.

Figure 2:
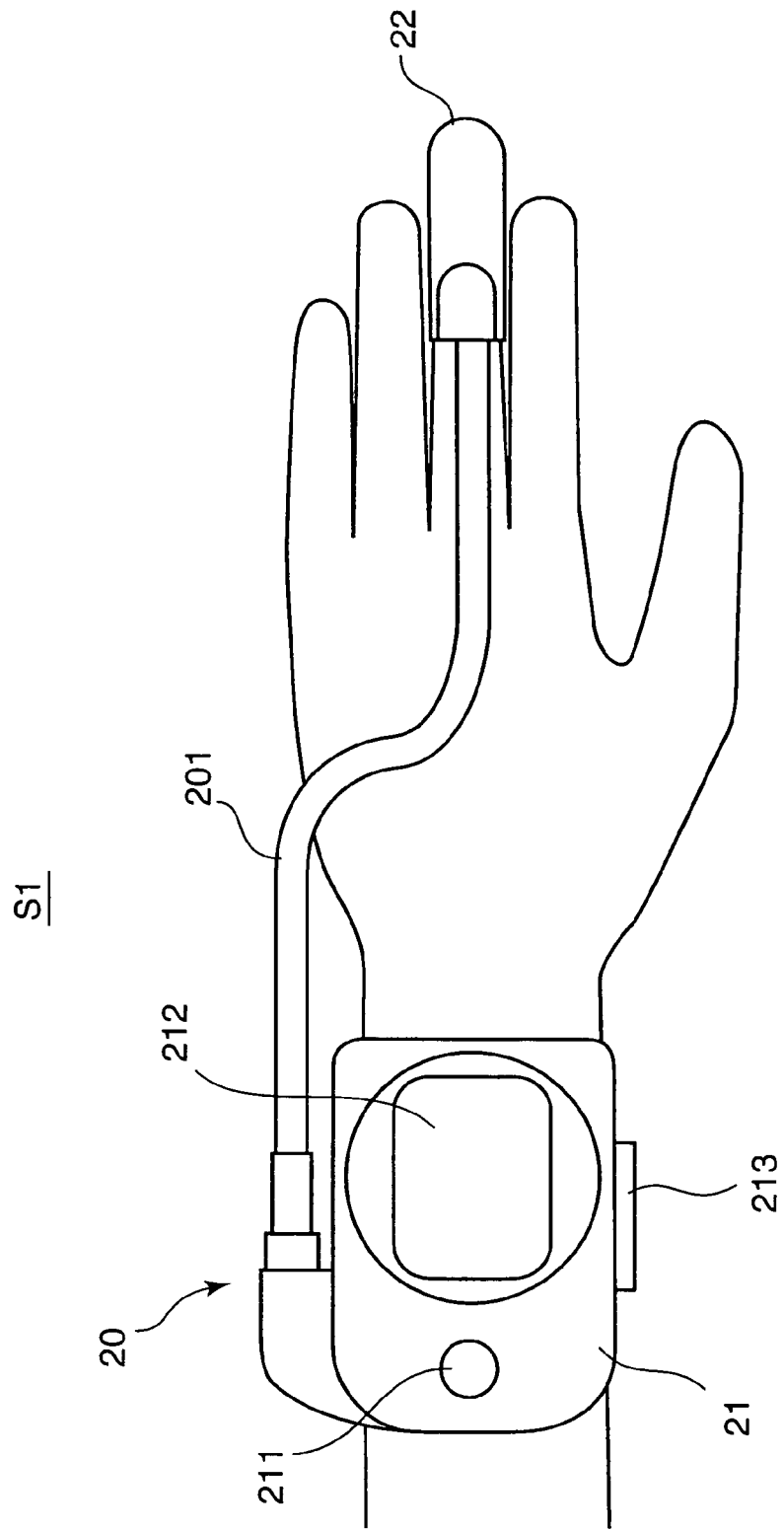
FIG. 2 is a diagram schematically showing one specific example of the hardware configuration of the pulse wave data analyzing system of FIG. 1.

The above-described pulse wave data analyzing system S0 can be constructed in various hardware constructions. FIG. 2 is a diagram schematically showing the hardware configuration of a pulse wave data analyzing system S1 which is one specific example of the pulse wave data analyzing system S0 of the embodiment built up as a pulse wave measuring apparatus 20 including the pulse wave sensor unit 11, the data analyzer unit 12, the display unit 13 and the storage unit 14 mentioned above in a single structure which can easily be worn by a subject. The pulse wave measuring apparatus 20 (pulse wave data analyzing system S1) includes a main pulse wave measuring unit 21 and a fingertip-mountable probe 22 which are electrically connected to each other by a signal cable 201 as shown in FIG. 2.

The main pulse wave measuring unit 21 is provided with a power switch 211, a display window 212 (corresponding to the aforementioned display unit 13) made of an LCD or the like, a wrist strap 213 and an internal electric circuit configured to perform part of functions of the pulse wave sensor unit 11 as well functions of the data analyzer unit 12 and the storage unit 14. The probe 22 includes a light-emitting element and a photosensitive element constituting part of the aforementioned pulse wave sensor unit 11. The pulse wave data analyzing system S1 is of a wearable single-unit construction featuring superb portability and compactness, yet providing all necessary functions.

Figure 3:
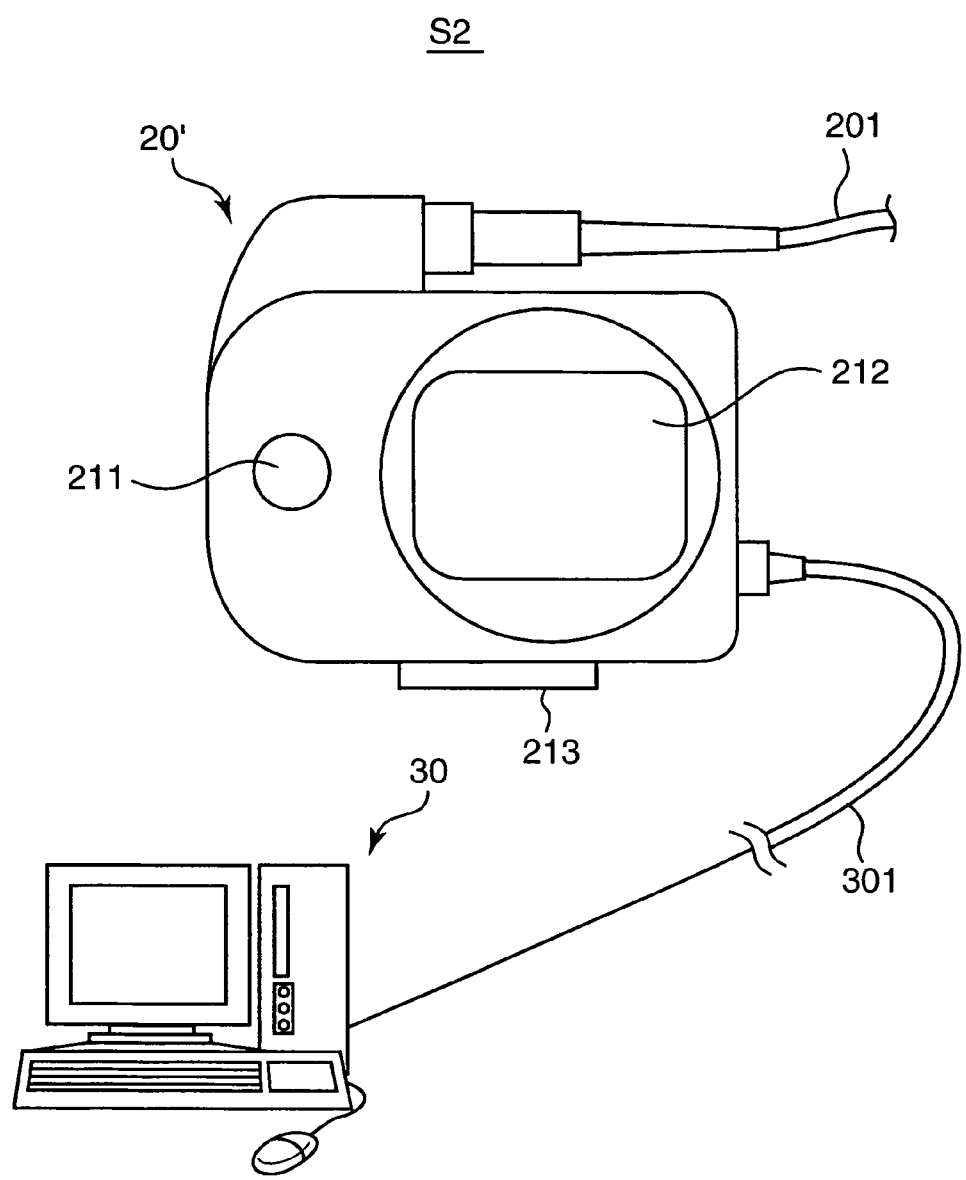
FIG. 3 is a diagram schematically showing another specific example of the hardware configuration of the pulse wave data analyzing system of FIG. 1.

FIG. 3 is a diagram schematically showing the hardware configuration of a pulse wave data analyzing system S2 which is another specific example of the system configuration according to the embodiment. The pulse wave data analyzing system S2 comprises a pulse wave measuring apparatus 20' (first device) wearable by the subject and a personal computer 30 (second device) which are connected to each other by a communications cable 301 (e.g., Universal Serial Bus, or USB, cable). In this pulse wave data analyzing system S2, the pulse wave measuring apparatus 20' performs the functions of the aforementioned pulse wave sensor unit 11 while the personal computer 30 performs those of the aforementioned data analyzer unit 12 and display unit 13. (Needless to say, the pulse wave measuring apparatus 20' may also be configured to perform the functions of the data analyzer unit 12 and the display unit 13.) This configuration of the pulse wave data analyzing system S2 is advantageous in that the pulse wave measuring apparatus 20' to be worn by the subject can be simplified in construction to provide improved ease of wearing and the personal computer 30 can be programmed to conduct more sophisticated analyses.

Figure 4:
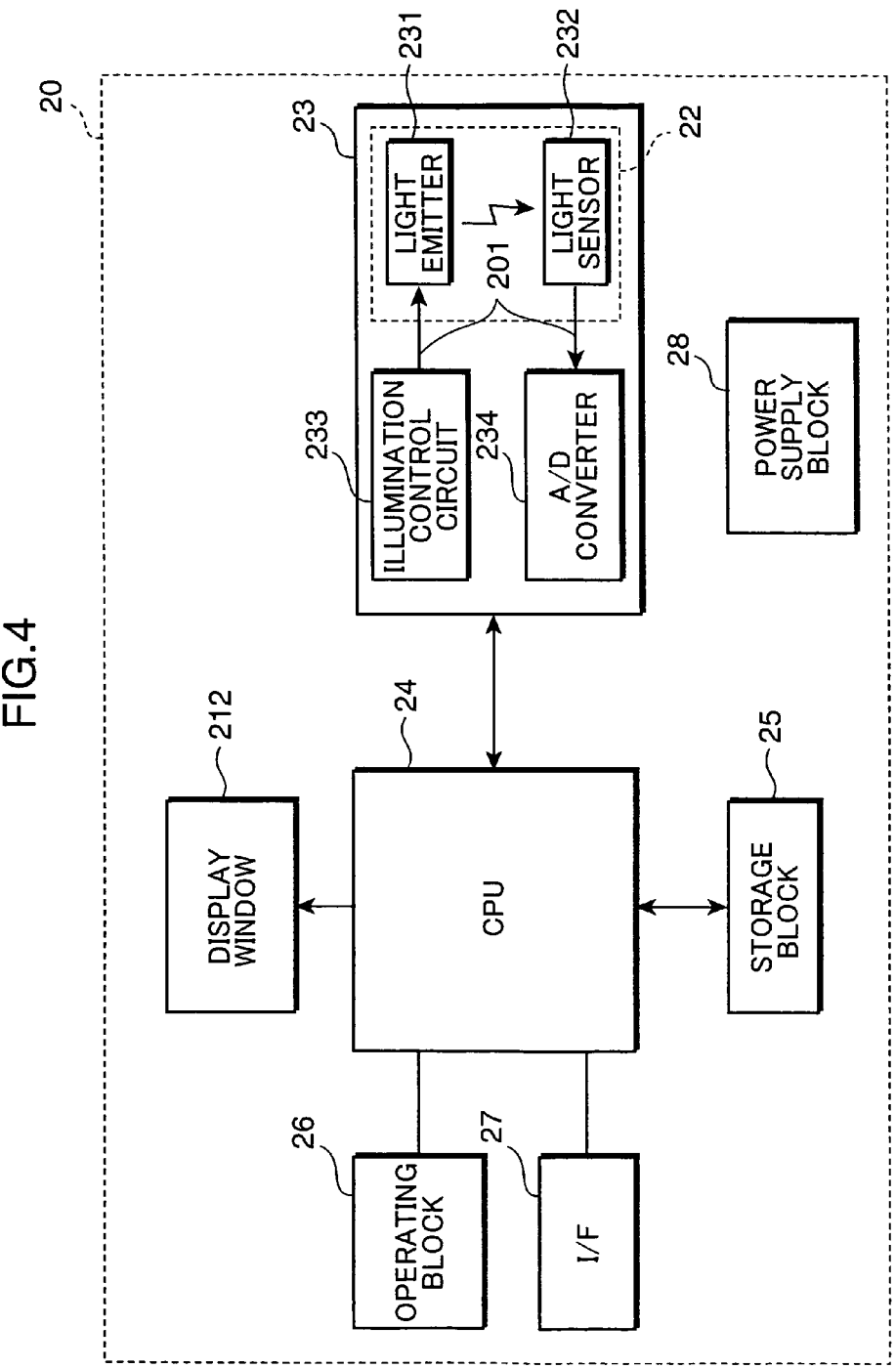
FIG. 4 is a block diagram showing the electrical configuration of the example of the pulse wave data analyzing system shown in FIG. 2.

FIG. 4 is a block diagram showing the electrical configuration of the pulse wave measuring apparatus 20 shown in FIG. 2. The pulse wave measuring apparatus 20 includes a sensor block 23 (pulse wave sensor), a CPU 24 (data analyzer), a storage block 25 (storage unit), an operating block 26, an interface block 27, a power supply block 28 and the aforementioned display window 212 (display unit).

The sensor block 23 is controlled by a later-described measurement control unit 41 of the CPU 24 to measure pulse wave information of the subject at the aforementioned specified sampling intervals (e.g., 30 ms). As shown in FIG. 4, the sensor block 23 includes a light emitter 231, a light sensor 232, an illumination control circuit 233 and an analog-to-digital (A/D) converter 234. The light emitter 231 and the light sensor 232 are built in the probe 22 while the illumination control circuit 233 and the A/D converter 234 are provided in the main pulse wave measuring unit 21, the light emitter 231 and the light sensor 232 being connected to the illumination control circuit 233 and the A/D converter 234 being electrically connected by the signal cable 201, respectively. The light emitter 231 and the light sensor 232 together constitute a reflected light or transmitted light sensor for measuring the pulse wave by using the light absorption characteristic of hemoglobin in the blood as mentioned earlier. The light emitter 231 and the light sensor 232 are disposed in the probe 22 to form a light path passing through a living body tissue (fingertip in this embodiment).

The light emitter 231 is a light source like an LED which emits light of a specific wavelength $\lambda$. Light-emitting operation of the light emitter 231 is controlled by the illumination control circuit 233 which generates a driving signal for lighting the light emitter 231 at the aforementioned specified sampling intervals according to a measurement control signal fed from the CPU 24. The light sensor 232 is a photoelectric conversion type photosensitive element having sensitivity to at least the light of the wavelength $\lambda$ emitted by the light emitter 231. The light sensor 232 generates a current corresponding to received light intensity. A known example of such a photosensitive element is a silicon photodiode. The A/D converter 234 converts an analog current corresponding to the received light intensity output from the light sensor 232 into a digital signal.

The amount of light (i.e., the amount of the reflected light or the transmitted light) received by the light sensor 232 varies with blood flow pulsation cycles. This is because the amount of absorbed light cyclically varies due to wavy changes in the amount of hemoglobin flowing through the blood vessels in the living body part under test as a result of the blood flow pulsation, or heartbeats. Accordingly, the digital signal corresponding to the amount of the received light output from the A/D converter 234 at the specified sampling intervals contains information reflecting conditions of the pulse wave over successive sampling cycles. The pulse wave information thus obtained is stored in association with time information in the storage block 25 through the CPU 24.

The CPU 24 performs overall control of the pulse wave measuring apparatus 20 according to particular control programs. More specifically, the CPU 24 controls pulse wave data acquisition operation performed by the sensor block 23, the aforementioned noise filtering operation for removing notch noise components contained in the raw pulse wave data obtained, and the aforementioned mathematical operation for determining intervals of top peaks (or bottom peaks) appearing on the pulse waveform based on the pulse wave data which has passed through the noise filtering operation. A detailed description of internal functional units of the CPU 24 will be given at a later time with reference to FIG. 5.

The storage block 25 (including later-described first to fourth storage units) temporarily stores the pulse wave data obtained by the sensor block 23, that is, digital data output from the A/D converter 234 associated with the time information, as well as data obtained as a result of the mathematical operation performed by the CPU 24, such as data classified as "temporarily erased data" and the results of analysis of the pulse wave data which may include top peak intervals, bottom peak intervals and bottom-to-top amplitude obtained by a later-described peak interval calculation unit 45.

The operating block 26 is provided with various switches (buttons) used for entering specific commands for operating individual system components. Specifically, the operating block 26 includes, in addition to the aforementioned power switch 211 (shown in FIG. 2) for turning on and off the power supply block 28, a measurement switch for causing the sensor block 23 to start and stop operation for detecting the pulse wave data and operation for analyzing the detected data. The switches provided in the operating block 26 may take various forms, such as mechanically operated pushbuttons or input buttons displayed on an LCD touch panel.

The interface block 27 used for data exchange to and from the personal computer 30 shown in FIG. 3, for example, is a data communications device for a wired network (e.g., local area network, or LAN) or a radio communications network configured using such a communications standard as RS-232C, USB or Infrared Data Association (IrDA) standard.

The power supply block 28 includes a dry cell or button cell battery or an AC power supply unit for supplying electric power to the individual system components. The display window 212 presents the results of analysis of the pulse wave data produced by the CPU 24 in the form of text information and/or image information, for instance.

The functional configuration of the CPU 24 and the storage block 25 is now described with reference to a functional block diagram of FIG. 5. The CPU 24 includes such functional units as the aforementioned measurement control unit 41, a data analyzer 42 and a display control unit 46. Also, the storage block 25 includes such functional units as a pulse wave data storage unit 251 (third storage unit), a peak value storage unit 252 (first storage unit), a temporarily erased data storage unit 253 (second storage unit) and an analysis result storage unit 254 (fourth storage unit).

The measurement control unit 41 is for controlling the pulse wave data acquisition operation. Specifically, the measurement control unit 41 generates an illumination control signal at the predetermined sampling intervals using an internal timer function and delivers the illumination control signal to the illumination control circuit 233 (FIG. 4). Also, the measurement control unit 41 receives the digital signal output from the A/D converter 234 in synchronism with the illumination control signal and writes the pulse wave information derived from the digital signal in the pulse wave data storage unit 251 of the storage block 25 in association with time information.

The display control unit 46 performs data processing operation for properly formatting the results of analysis of the pulse wave data produced by the CPU 24 and displaying the results of analysis of the pulse wave data thus formatted on the display window 212.

The data analyzer 42 performs various kinds of data analyzing operation on the pulse wave data acquired by the sensor block 23 and once stored in the storage block 25 (or directly on the pulse wave data detected by the sensor block 23). The data analyzer 42 includes a preprocessing block 43, a noise filtration block 44 and the aforementioned peak interval calculation unit 45.

The preprocessing block 43 is a functional block including a pulse waveform generating unit 431 and a moving average processing unit 432 which together carry out particular preprocessing operation on the raw pulse wave data acquired by the sensor block 23 prior to the notch noise filtering operation performed by the noise filtration block 44.

The pulse waveform generating unit 431 generates a pulse waveform 51 (FIG. 6) by performing pulse wave data arrangement operation. Specifically, the pulse waveform generating unit 431 arranges values of the pulse wave data acquired at the predetermined sampling intervals and stored in the pulse wave data storage unit 251 in association with time information along the time axis. In a case where the pulse wave data is to be analyzed in real time while the same is being measured, the preprocessing block 43 performs successive readout operation to sequentially read out successive data values which are written in the pulse wave data storage unit 251 with the progress of wave data measurement cycles.

The moving average processing unit 432 performs moving average processing operation on the pulse waveform generated by the pulse waveform generating unit 431 to smooth out the same. For example, the moving average processing unit 432 sequentially calculates moving averages of five successive pulse wave data values plotted along the time axis of the pulse waveform, wherein each of the moving averages is an average of the pulse wave data values at a central sampling point and at two each immediately preceding and following sampling points. A reason why the moving average processing unit 432 performs such moving average processing operation is as follows.

Figure 6:
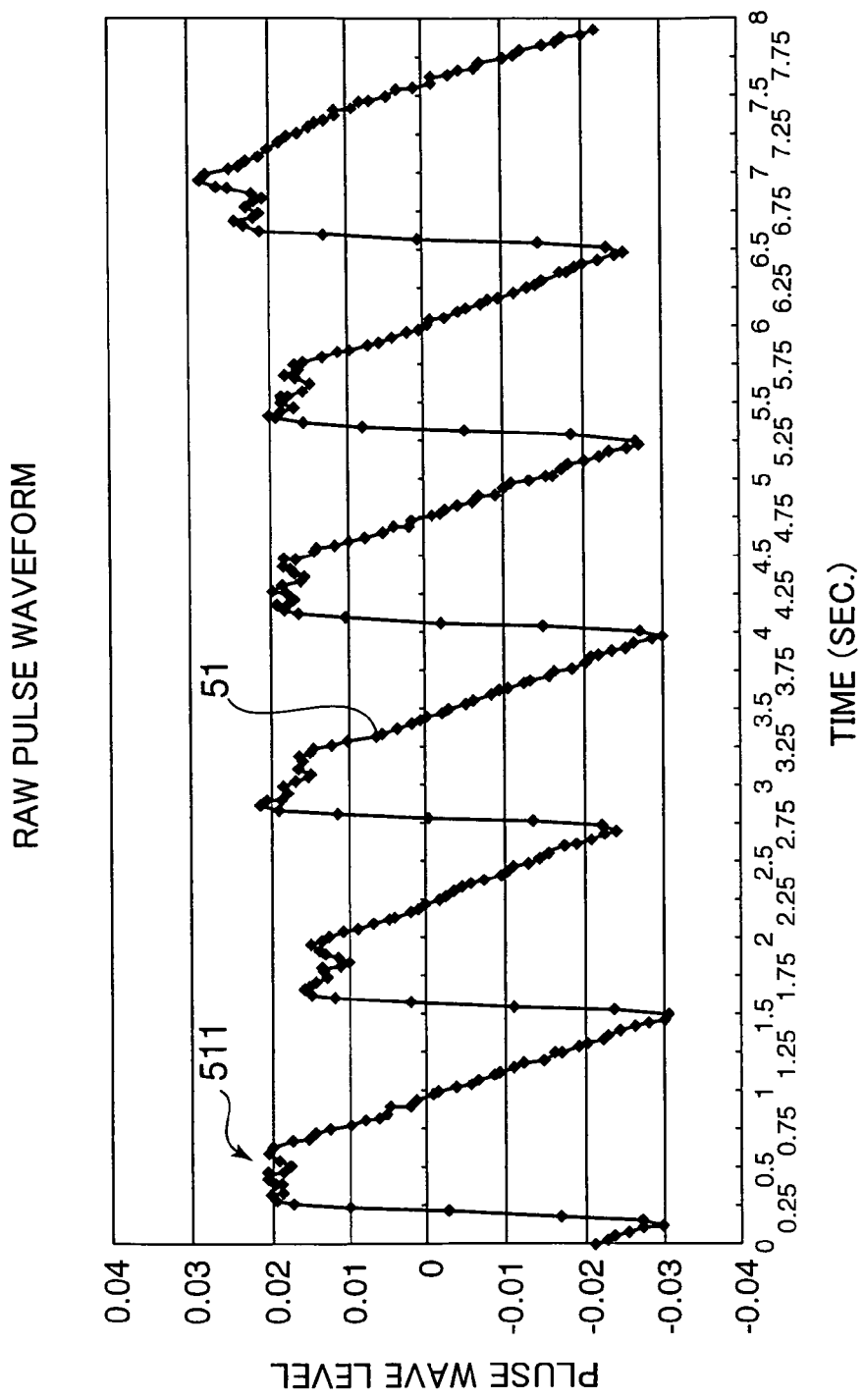
FIG. 6 is a graph showing a raw pulse waveform produced by a pulse waveform generating unit provided in a preprocessing block of the CPU.

FIG. 6 is a graph showing the pulse waveform 51 produced by the pulse waveform generating unit 431 at the aforementioned sampling intervals (=26.7 ms in FIG. 6). The pulse waveform 51 shown in FIG. 6 is an example of a raw pulse waveform obtained by plotting the raw pulse wave data. This kind of raw pulse waveform 51 often contains noise components as in a portion marked by the numeral 511 in FIG. 6 which occur within an extremely short period of time and are superimposed on the pulse wave data. Since these noise components might be regarded as a sort of bottom and top peaks, the noise components occurring in the raw pulse wave data could hinder high-speed processing, in one way or another, if the noise filtration block 44 performs the noise filtering operation for removing notch noise components from the raw pulse waveform 51.

Figure 7:
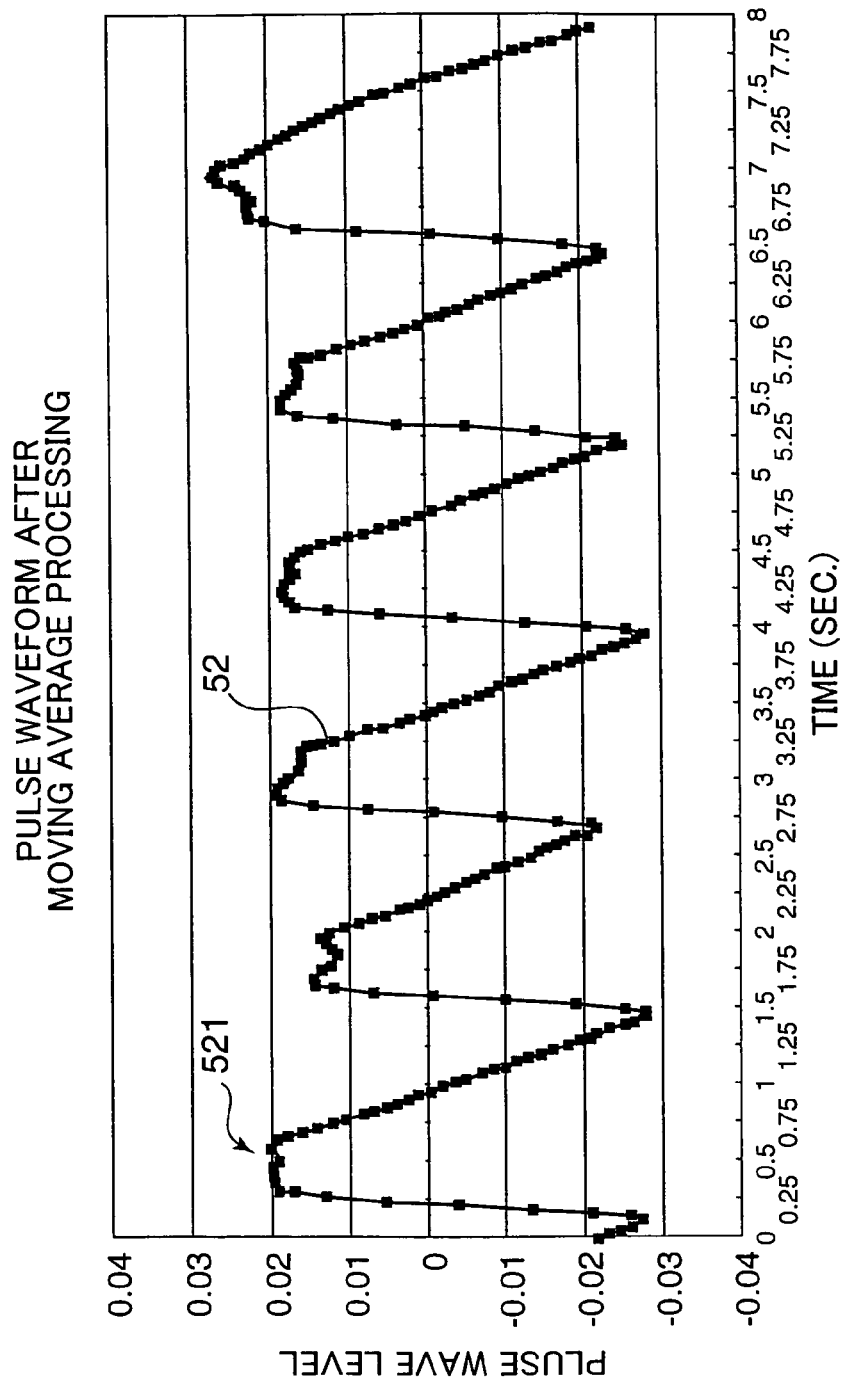
FIG. 7 is a graph showing a pulse waveform smoothed by moving average processing operation.

Under such circumstances, the moving average processing unit 432 performs the aforementioned moving average processing operation on the raw pulse waveform 51 to smooth out the same. FIG. 7 is a graph showing a pulse waveform 52 smoothed by moving average processing operation, wherein a portion of the pulse waveform 52 designated by the numeral 521 corresponds to the portion of the pulse waveform 51 designated by the numeral 511 in FIG. 6. It can be seen from FIGS. 6 and 7 that this portion is smoothed by the moving average processing operation, which serves to simplify a succeeding process of extracting bottom and top peak values performed by the noise filtration block 44.

The noise filtering operation performed by the noise filtration block 44 is for removing notch noise components contained in the pulse waveform 52 shown in FIG. 7 which has been smoothed by the moving average processing operation. The noise filtration block 44 includes an inflection point detecting unit 441, an amplitude detecting unit 442, a temporary erasure unit 443 and a noise filtration unit 444.

Figure 8:
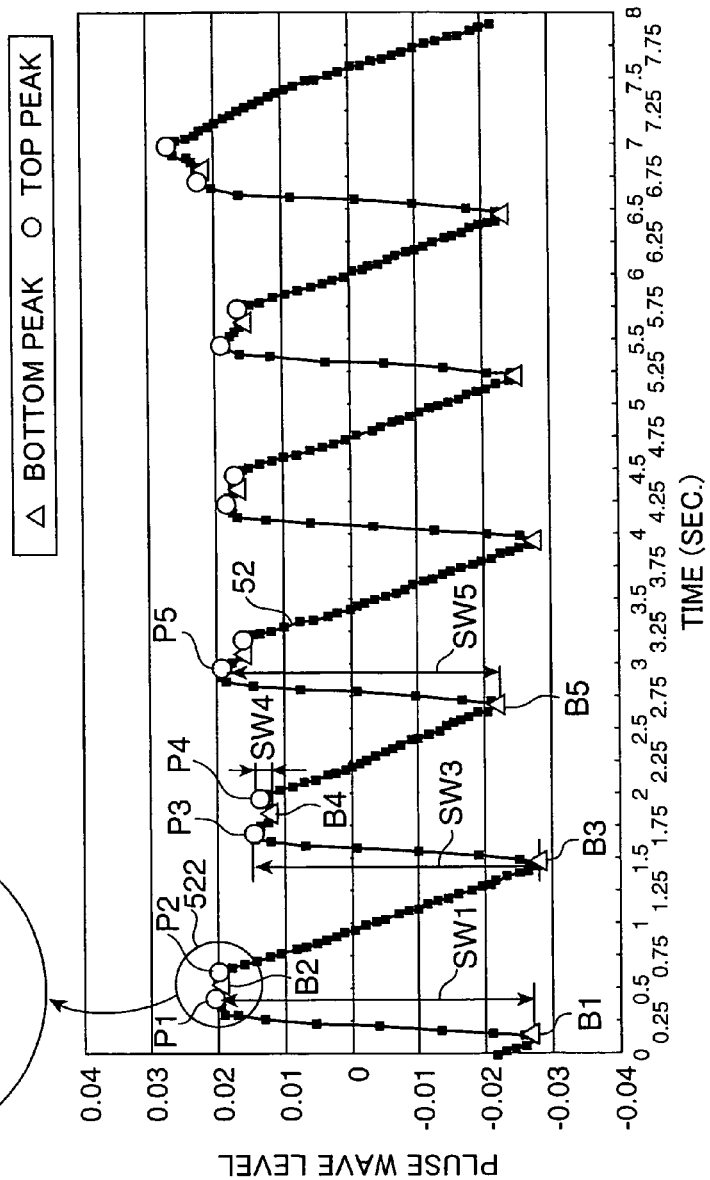
FIG. 8 is a graph showing an example of bottom and top peaks of the pulse waveform detected by a data analyzer of the CPU.

The inflection point detecting unit 441 performs operation for successively detecting bottom and top peak values occurring on the pulse waveform 52 (pulse wave data) shown in FIG. 7 which has been smoothed by the moving average processing operation. Specifically, the inflection point detecting unit 441 compares successive pulse wave data values plotted to form the pulse waveform 52 along the time axis and detects a point where the gradient of the pulse waveform 52 changes from negative to positive as a bottom peak and a point where the gradient of the pulse waveform 52 changes from positive to negative as a top peak. FIG. 8 is a graph showing an example of bottom and top peaks of the pulse waveform 52 detected by the inflection point detecting unit 441, wherein the symbols B1 to B5 designate the bottom peaks and the symbols P1 to P5 designate the top peaks. In a case where the pulse wave data is to be analyzed in real time, the inflection point detecting unit 441 compares successive pulse wave data values and detects the bottom and top peak values while successively acquiring pulse wave data values of the pulse waveform 52. The bottom and top peak values thus detected are stored in the peak value storage unit 252 of the storage block 25.

Using the bottom peak values B1-B5 and the top peak values P1-P5 detected by the inflection point detecting unit 441, the amplitude detecting unit 442 performs operation for combining two adjacent bottom and top peak values occurring in succession along the time axis in pairs and calculating a bottom-to-top amplitude value which is a difference between the bottom and top peak values of each successive pair along the time axis. This processing operation is described more specifically with reference to FIG. 8. In the beginning, the amplitude detecting unit 442 pairs the bottom peak value B1 and the top peak value P1 (refer to an enlarged view of a portion of the pulse waveform 52 designated by the numeral 522) and calculates a difference between the bottom peak value B1 and the top peak value P1 to obtain a first bottom-to-top amplitude value SW1. Similarly, the amplitude detecting unit 442 pairs the bottom peak value B2 and the top peak value P2, the bottom peak value B3 and the top peak value P3, the bottom peak value B4 and the top peak value P4 and the bottom peak value B5 and the top peak value P5, and calculates differences between the respective bottom and top peak values to obtain second to fifth bottom-to-top amplitude values SW2-SW5. The amplitude detecting unit 442 performs the same processing operation on the bottom and top peak values whichever occurring after the bottom peak value B5 and the top peak value P5.

The temporary erasure unit 443 compares a first peak-to-peak amplitude value AM1 and a second peak-to-peak amplitude value AM2 occurring in succession along the time axis that correspond respectively to the first bottom-to-top amplitude value SW1 and the second bottom-to-top amplitude value SW2, for example. Then, if the ratio of the second bottom-to-top amplitude value SW2 to the first bottom-to-top amplitude value SW1 is smaller than a preset threshold, the temporary erasure unit 443 temporarily transfers the bottom peak value B2 and the top peak value P2 related to the second bottom-to-top amplitude value SW2 from the peak value storage unit 252 to the temporarily erased data storage unit 253 to classify the bottom peak value B2 and the top peak value P2 as temporarily erased data. Specifically, the temporary erasure unit 443 performs mathematical operation shown by inequality (1) below (wherein AM1=SW1, AM2=SW2) and, if inequality (1) is satisfied, reserves the bottom peak value B2 and the top peak value P2 related to the second bottom-to-top amplitude value SW2 as temporarily erased data:

$$(\text{first peak-to-peak amplitude value } AM1) \times (\text{reference ratio ``}a\text{''}) > (\text{second peak-to-peak amplitude value } AM2) \quad (1)$$

where the reference ratio "a" has an arbitrarily preset value equal to or smaller than 1.

While the reference ratio "a" (preset threshold) used in inequality (1) above is set as appropriate according to heart-beat characteristics of the subject and expected symptoms, notch noise is usually much lower than the heartbeat. Since the bottom-to-top amplitude value of the notch noise is typically about 50% or less relative to the bottom-to-top amplitude value of true pulse waves, it is possible to set the reference ratio "a" at a default value of 0.5 ("a"=0.5), for example.

Next, the temporary erasure unit 443 compares the first bottom-to-top amplitude value SW1 with the third bottom-to-top amplitude value SW3 derived from the bottom peak value B3 and the top peak value P3 which occur following the bottom peak value B2 and the top peak value P2 which have been temporarily erased as mentioned above. Specifically, substituting the third bottom-to-top amplitude value SW3 for the second peak-to-peak amplitude value AM2 in inequality (1) above (AM2=SW3), the temporary erasure unit 443 performs the same mathematical operation as described above.

For the purpose of the following discussion it is now assumed that the reference ratio "a" is preset at "a"=0.5 with respect to the pulse waveform 52 shown in FIG. 8. Since SW1>>SW2 in the example of FIG. 8, the temporary erasure unit 443 temporarily erases the bottom peak value B2 and the top peak value P2 related to the second bottom-to-top amplitude value SW2. Then, the temporary erasure unit 443 compares SW1 and SW3. As is apparent from FIG. 8, SW1× 0.5<SW3 so that the bottom peak value B3 and the top peak value P3 related to the third bottom-to-top amplitude value SW3 are not temporarily erased but held in the peak value storage unit 252.

Subsequently, the temporary erasure unit 443 uses SW3 which has not been temporarily erased as a new first peak-to-peak amplitude value AM1 and repeats the aforementioned mathematical operation. Specifically, substituting the fourth bottom-to-top amplitude value SW4 for the second peak-to-peak amplitude value AM2 in inequality (1) above (AM2=SW4), the temporary erasure unit 443 judges whether a condition expressed by inequality SW3×(reference ratio "a")>SW4 is satisfied. Since SW3>>SW4 in the example of FIG. 8, the temporary erasure unit 443 transfers the bottom peak value B4 and the top peak value P4 related to the fourth bottom-to-top amplitude value SW4 to the temporarily erased data storage unit 253 to classify the values B4, P4 as temporarily erased data. Further, the temporary erasure unit 443 judges whether a condition expressed by inequality SW3× (reference ratio "a")>SW5 is satisfied and, as a result, the bottom peak value B5 and the top peak value P5 related to the fifth bottom-to-top amplitude value SW5 are held in the peak value storage unit 252.

If the result of the aforementioned comparison between SW1 and SW3 is SW1×0.5>SW3, the temporary erasure unit 443 temporarily erases the bottom peak value B3 and the top peak value P3 as well and compares SW1 and SW4. In this case, the temporary erasure unit 443 decreases the reference ratio "a" to a smaller value (e.g., "a"=0.1) and makes the aforementioned comparison. This is because, if SW3 has a large value for some reason and the comparison is made by using the reference ratio "a" of 0.5 ("a"=0.5), for example, peak value data occurring after SW1 will be successively erased regardless of whether the peak values represent true pulse waves, and not notch noise. Also, from the same point of view, the number m of repetitive comparisons made by using the first bottom-to-top amplitude value SW1 as a reference is limited to a particular number (e.g., m=5). When this number of repetitive comparisons is exceeded, the temporary erasure unit 443 forcibly substitutes a next bottom-to-top amplitude value for the first peak-to-peak amplitude value AM1. The above-described operation performed by the temporary erasure unit 443 of the present embodiment is desirable for execution of pulse wave measurement and real-time pulse wave data analysis.

The noise filtration unit 444 compares the temporarily erased second peak-to-peak amplitude value AM2 with a third peak-to-peak amplitude value AM3 which occurs in succession to the second peak-to-peak amplitude value AM2 on the time axis, and judges whether the ratio between the two values AM2, AM3 is larger than the preset threshold, which may be the aforementioned reference ratio "a" of 0.5 ("a"=0.5), for example, at this point. In the case of the pulse waveform 52 shown in FIG. 8, the temporarily erased second bottom-to-top amplitude value SW2 and the third bottom-to-top amplitude value SW3 occurring in succession thereto on the time axis are compared. Since the value SW3 is larger than the value SW2 in the example of FIG. 8, the noise filtration unit 444 judges whether a condition expressed by inequality SW3×(reference ratio "a")>SW2 is satisfied. If the condition of this inequality is satisfied, SW2 gives only a bottom-to-top amplitude value which is sufficiently small as compared not only to the preceding value SW1 but also to the succeeding value SW3, indicating that there is extremely large likelihood that the second bottom-to-top amplitude value SW2 represents a notch noise component.

Therefore, when the condition of the aforementioned inequality is satisfied, the noise filtration unit 444 regards the bottom peak value B2 and the top peak value P2 related to the second bottom-to-top amplitude value SW2 as notch noise components and completely erases these peak values B2, P2. More specifically, the noise filtration unit 444 completely erases the bottom peak value B2 and the top peak value P2 from the temporarily erased data storage unit 253. When the condition of the aforementioned inequality is not satisfied, on the other hand, classification of the bottom peak value B2 and the top peak value P2 related to the second bottom-to-top amplitude value SW2 as temporarily erased data is canceled and these peak values B2, P2 are treated as data to be used for pulse wave data analysis. Specifically, the noise filtration unit 444 restores the bottom peak value B2 and the top peak value P2 by transferring the peak values B2, P2 from the temporarily erased data storage unit 253 back to the peak value storage unit 252. Since SW3>>SW2 in the case of the pulse waveform 52 shown in FIG. 8, the noise filtration unit 444 completely erases the bottom peak value B2 and the top peak value P2 related to the second bottom-to-top amplitude value SW2.

Figure 9:
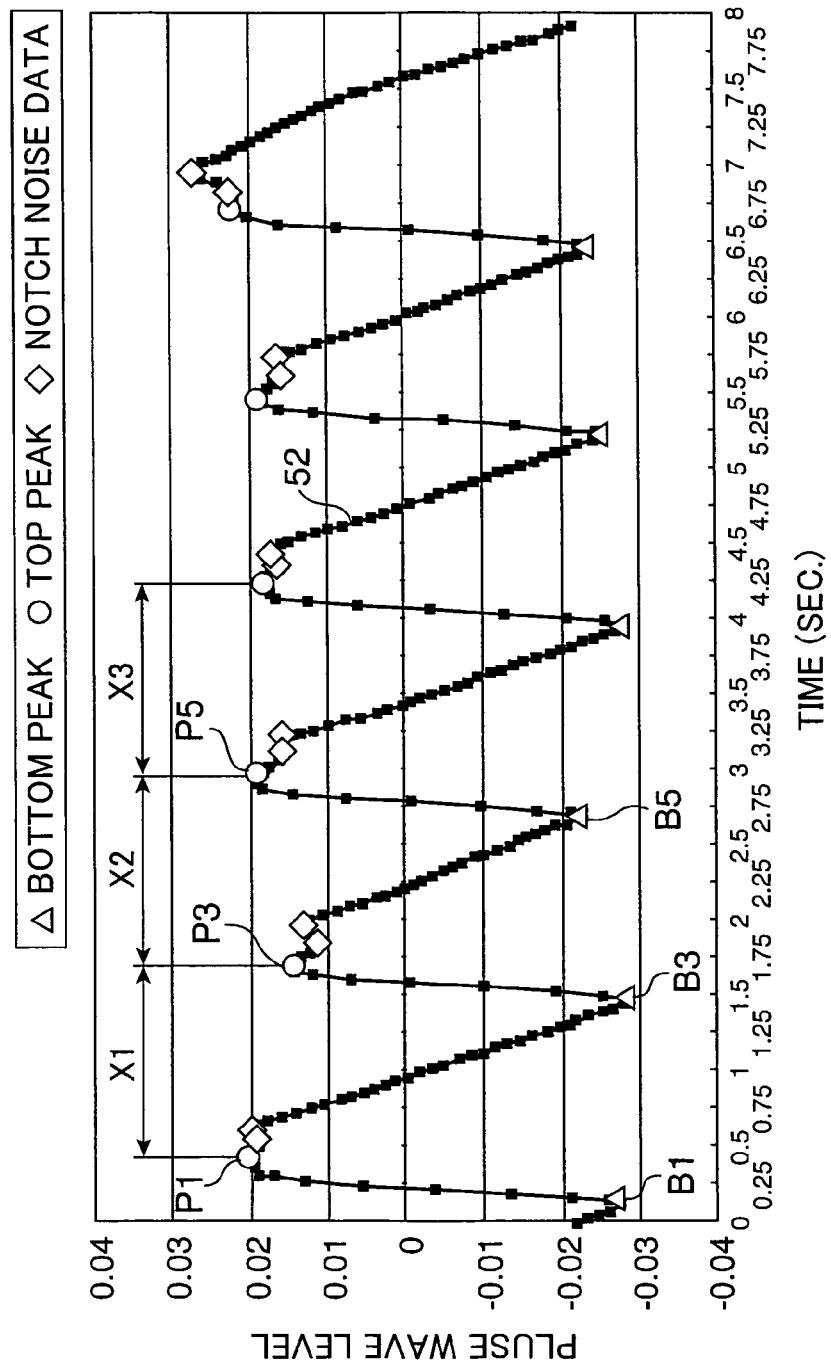
FIG. 9 is a graph showing the pulse waveform from which notch noise has been erased.

Bottom and top peak values of the pulse waveform 52 shown in FIG. 8 that are left in the peak value storage unit 252 without being erased by the above-described operation performed by the noise filtration unit 444 are the bottom peak values B1, B3, B5 and the top peak values P1, P3, P5. This means that, as can be seen from FIG. 9, the bottom peak values B2, B4 and the top peak values P2, P4 regarded as notch noise components have been erased while the bottom peak values B1, B3, B5 and the top peak values P1, P3, P5 related to true heartbeats are left for analysis. It is then possible to accurately calculate the PP interval by determining a time interval X1 between the top peak values P1 and P3, a time interval X2 between the top peak values P3 and P5, and so on. Needless to say, the PP interval can be obtained by determining time intervals between the bottom peak values B1 and B3, B3 and B5, and so on instead of determining the time intervals X1, X2, and so on.

Figure 10:
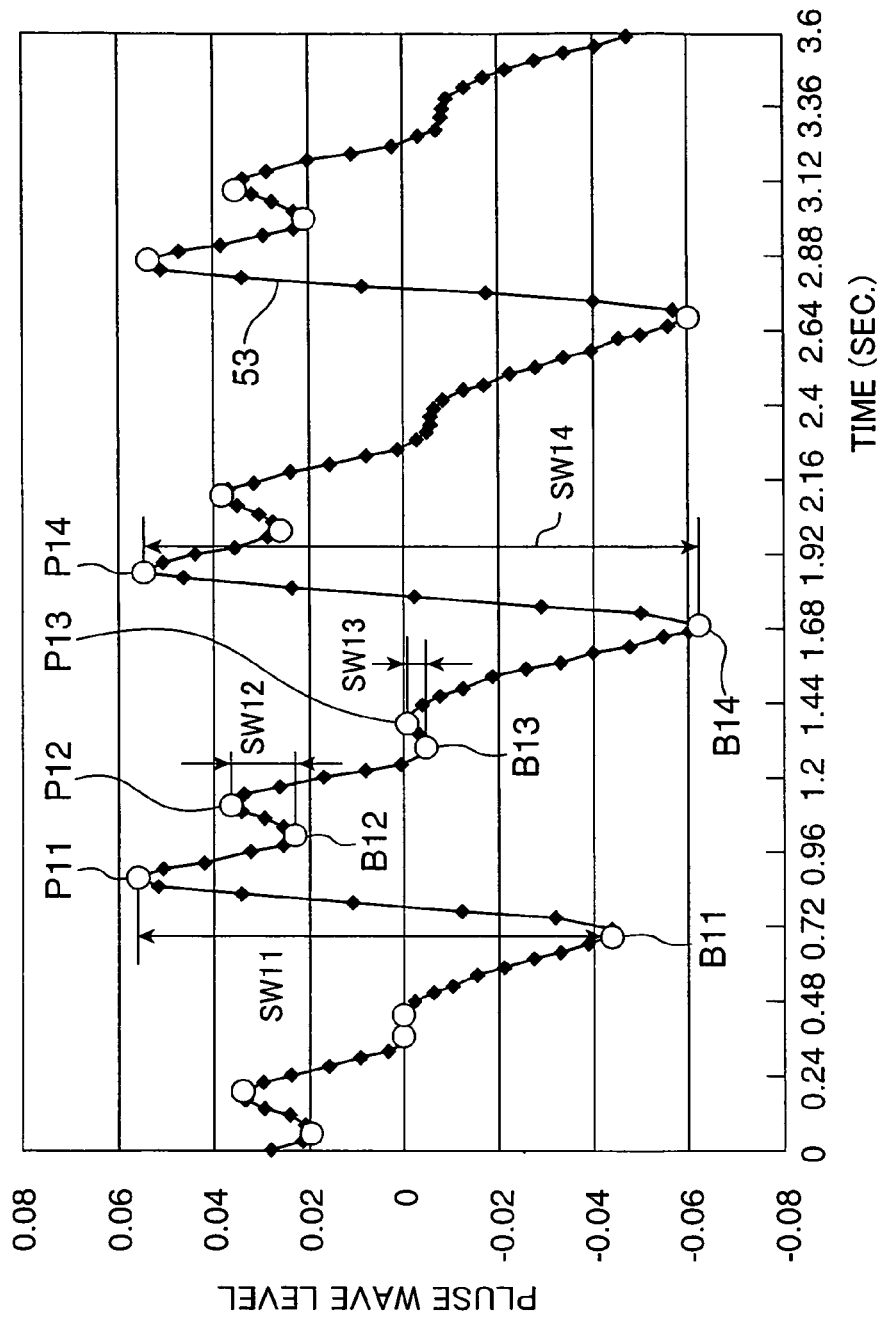
FIG. 10 is a graph showing another pulse waveform.

Generally, a detected pulse wave exhibits a wide variety of waveform patterns. From another pulse waveform 53 graphed in FIG. 10, the inflection point detecting unit 441 detects bottom peak values B11-B14 and top peak values P11-P14 and the amplitude detecting unit 442 determines first to fourth bottom-to-top amplitude values SW11-SW14. In this example, there exist two peaks producing small bottom-to-top amplitude values between the first and fourth bottom-to-top amplitude values SW11, SW14 which are large enough. These two small peaks presumably caused by notch noise are represented by the second and third bottom-to-top amplitude values SW12, SW13 in FIG. 10.

Since SW11>>SW12 and SW11>>SW13 in this pulse waveform 53, the temporary erasure unit 443 temporarily erases the bottom peak values B12, B13 and the top peak values P12, P13 related to the bottom-to-top amplitude values SW12 and SW13, respectively. On the other hand, the fourth bottom-to-top amplitude value SW14 is slightly larger than the first bottom-to-top amplitude value SW11 so that the bottom peak value B14 and the top peak value P14 related to the fourth bottom-to-top amplitude value SW14 are not temporarily erased and, then, the temporary erasure unit 443 uses SW14 as a reference value (first peak-to-peak amplitude value AM1) in performing the aforementioned comparison operation. Subsequently, the noise filtration unit 444 compares SW14 and SW12, and then SW14 and SW13. Since SW14>>SW12 and SW14>>SW13 in this example, the noise filtration unit 444 completely erases the bottom peak values B12, B13 and the top peak values P12, P13 related to SW12 and SW13, respectively.

Figure 11:
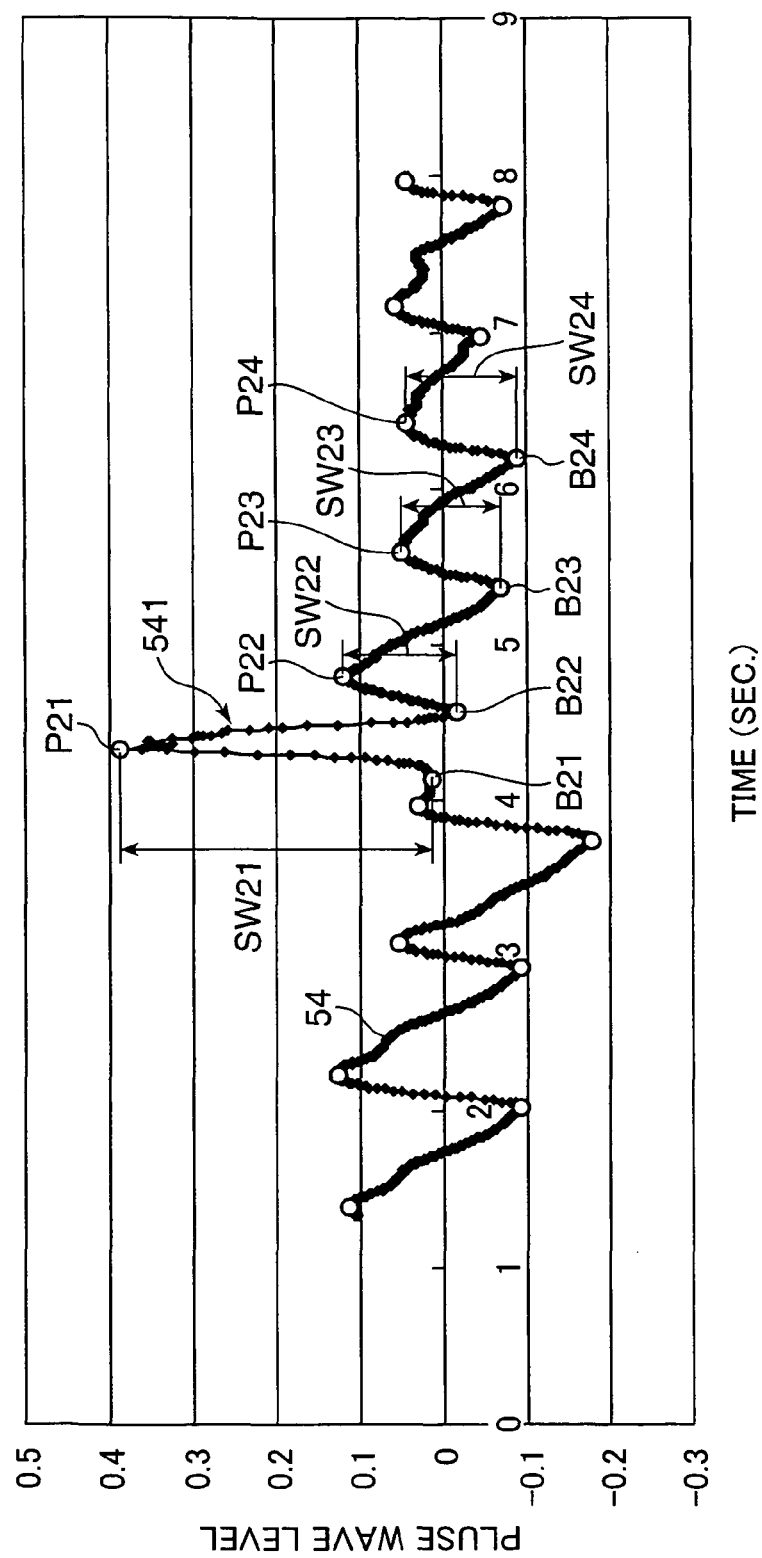
FIG. 11 is a graph showing still another pulse waveform.

Shown in FIG. 11 is a still another pulse waveform 54 which is an example containing an erratically rising large peak portion 541. This kind of erratically large peak portion 541 is caused by a sudden bodily movement of the subject, for instance, in most cases. The provision of the temporary erasure unit 443 and the noise filtration unit 444 of the present embodiment is significantly advantageous for processing this kind of pulse waveform 54.

From the pulse waveform 54 graphed in FIG. 11, the inflection point detecting unit 441 detects bottom peak values B21-B24 and top peak values P21-P24 that occur at and after the large peak portion 541 and the amplitude detecting unit 442 determines first to fourth bottom-to-top amplitude values SW21-SW24. In this example, SW21 represents an extraordinarily large bottom-to-top amplitude value while SW22-SW24 represent bottom-to-top amplitude values of ordinary pulse waves.

With this kind of pulse waveform 54, the temporary erasure unit 443 first sets SW21 as the first peak-to-peak amplitude value AM1 and SW22 as the second peak-to-peak amplitude value AM2 (AM1=SW21, AM2=SW22), and judges whether a condition expressed by inequality SW21×(reference ratio "a")>SW22 is satisfied, where "a"=0.5. In this case, SW21>>SW22 so that the condition of the above inequality is satisfied and, thus, the temporary erasure unit 443 temporarily erases the bottom peak value B22 and the top peak value P22 related to the fourth bottom-to-top amplitude value SW22. Next, the temporary erasure unit 443 sets SW23 as the second peak-to-peak amplitude value AM2 and judges whether a condition expressed by inequality SW21× 0.5>SW23 is satisfied. Since SW21>>SW23, the temporary erasure unit 443 temporarily erases the bottom peak value B23 and the top peak value P23 related to the fourth bottom-to-top amplitude value SW23 as well. Since a next step is a third comparison operation using SW21 as the reference value, the temporary erasure unit 443 decreases the reference ratio "a" to 0.1 ("a"=0.1) as mentioned earlier. Then, the temporary erasure unit 443 judges whether a condition expressed by inequality SW21×0.1>SW24 is satisfied. Since SW21 and SW24 do not satisfy this condition the temporary erasure unit 443 does not temporarily erase the bottom peak value B24 and the top peak value P24 related to the fourth bottom-to-top amplitude value SW24 and varies the first peak-to-peak amplitude value AM1 to SW24 (AM1=SW24) for a next comparison operation.

If SW22 and SW23 are evaluated by only the comparison operation using SW21 as the reference value, SW22 and SW23 derived from ordinary pulse waves will be misevaluated as noise and completely erased when SW21 is an extraordinarily large erratic bottom-to-top amplitude value as in the example of FIG. 11. It follows that, if the bottom peak values B22, B23 and the top peak values P22, P23 related respectively to the bottom-to-top amplitude values SW22 and SW23 are completely erased without the aforementioned process of temporary erasure and reevaluation, results of PP interval measurement will be greatly influenced.

Figure 12:
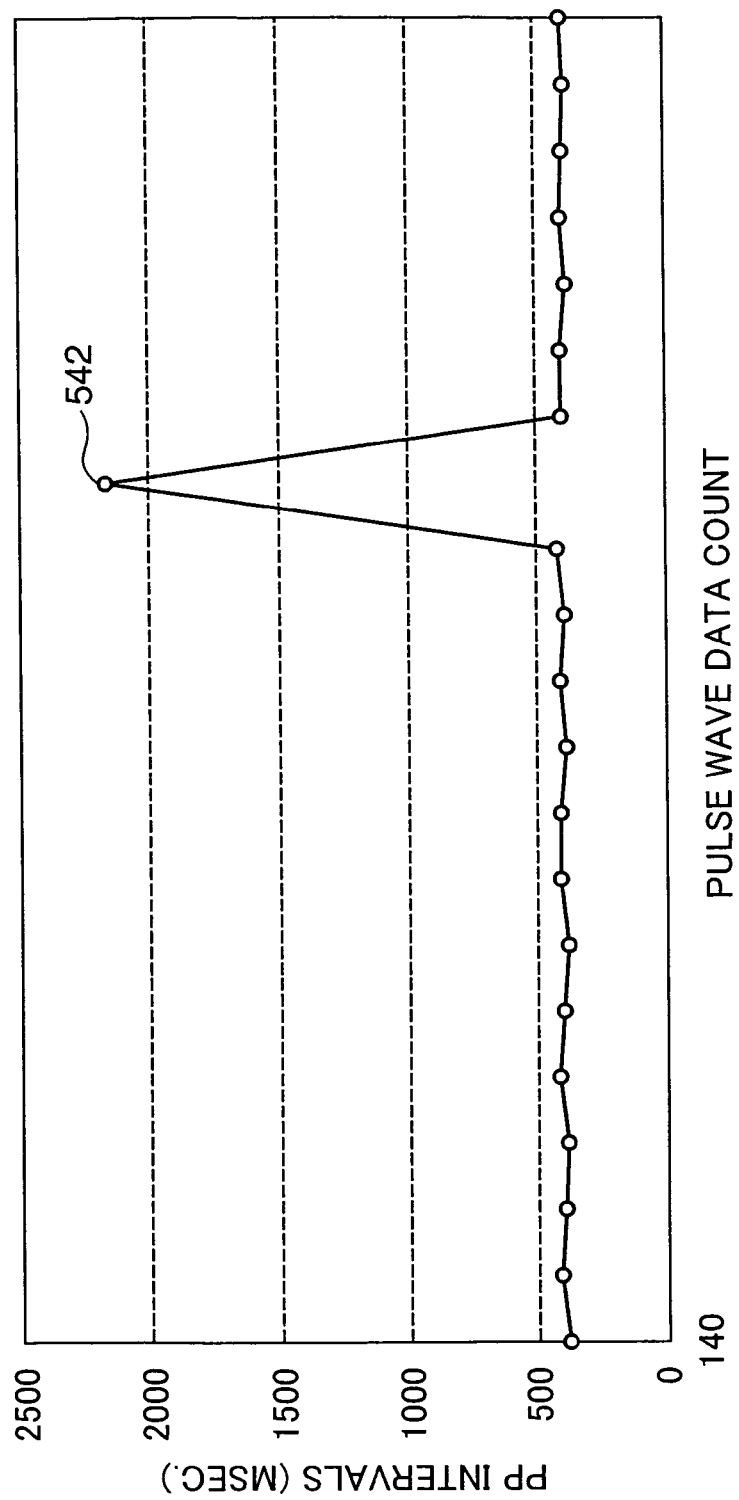
FIG. 12 is a graph showing how PP intervals measured at successive pulse wave data points of the pulse waveform of FIG. 11 vary.

FIG. 12 is a graph showing how PP intervals measured at successive pulse wave data points of the pulse waveform 54 of FIG. 11 vary. If the top peak values P22, P23 shown in FIG. 11 are erased as being notch noise, for example, the peak interval calculation unit 45 will calculate the interval between top peak values P1 and P2 as a PP interval value designated by the numeral 542 in FIG. 12, although this PP interval value 542 actually represents the sum of three successive PP intervals from P21 to P24. A medical worker may misinterpret this kind of erratic variations in PP intervals as a symptom of arrhythmia of the subject.

Figure 13:
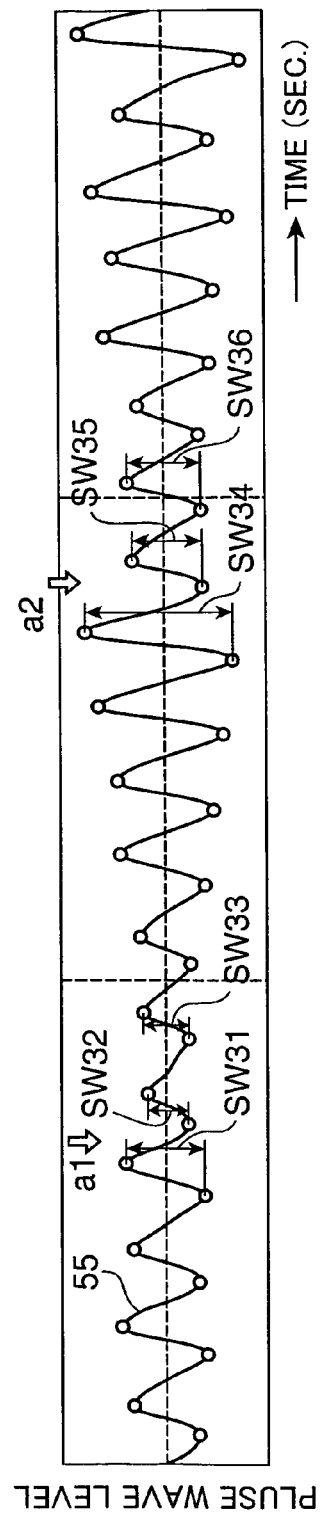
FIG. 13 is a graph showing a pulse waveform containing respiratory pulse wave amplitude variations.

A similar problem in pulse wave measurement can occur not only due to bodily movements of the subject but also in the presence of respiratory variations in pulse wave amplitude. FIG. 13 is a graph showing an example of a pulse waveform 55 containing respiratory pulse wave amplitude variations marked by arrows a1 and a2. Pulse wave amplitude variations of this kind occur with inhalation and exhalation cycles of the subject and become prominent at portions of transit from one respiratory cycle to the next marked by the arrows a1, a2.

Referring to FIG. 13, the amplitude detecting unit 442 calculates bottom-to-top amplitude values SW31-SW36 from this pulse waveform 55. Of the bottom-to-top amplitude values SW31-SW33 detected in the vicinity of the arrow a1, the bottom-to-top amplitude values SW32 and SW33 are approximately half the bottom-to-top amplitude value SW33 (where SW32<SW33). If the temporary erasure unit 443 sets SW31 as the first peak-to-peak amplitude value AM1 (AM1=SW31) and performs a comparison operation using the reference ratio "a" of 0.5 ("a"=0.5) in this case, SW32 may potentially be misjudged as noise, for example. A similar situation could also occur with the bottom-to-top amplitude values SW34-SW36 detected in the vicinity of the arrow a2. For example, SW35 may potentially be misjudged as noise.

Figure 14:
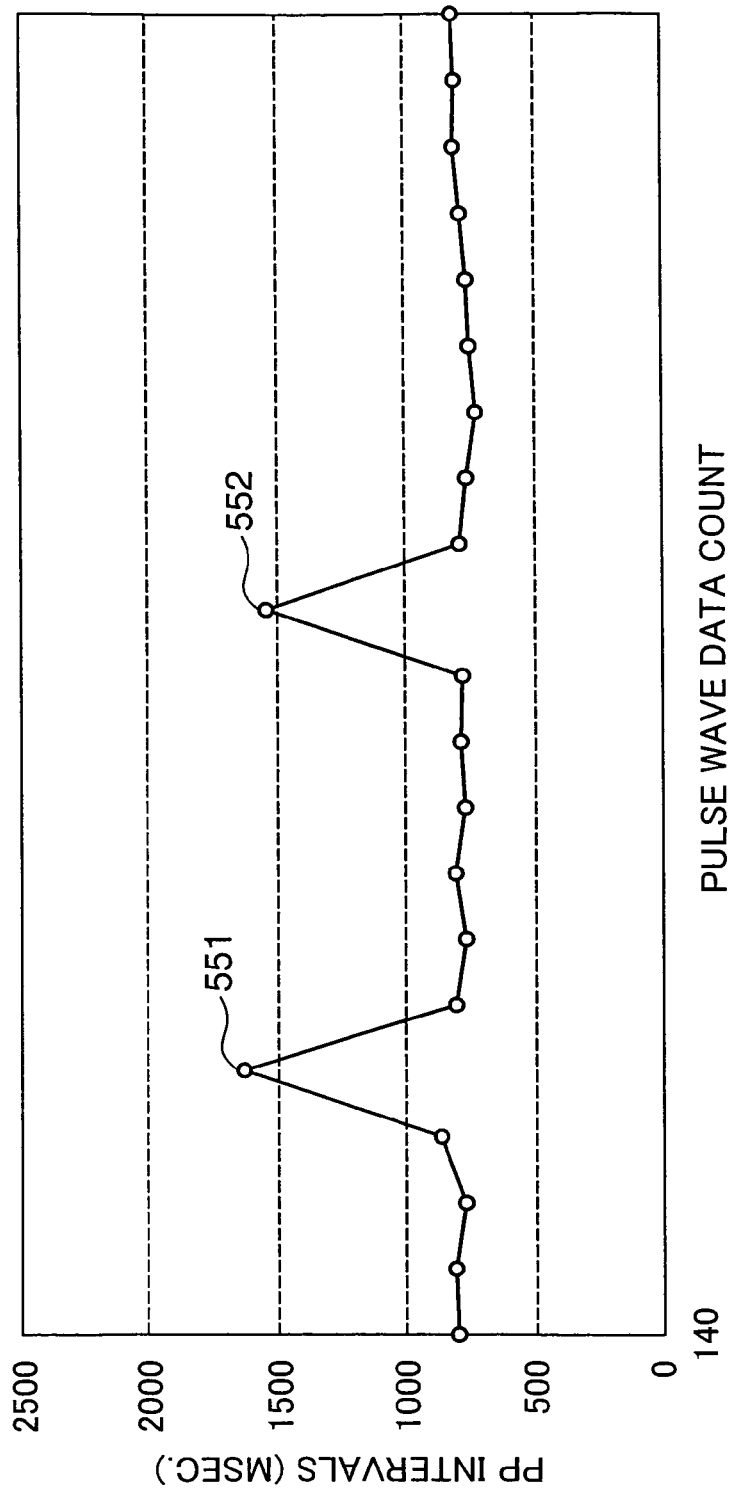
FIG. 14 is a graph showing how PP intervals measured at successive pulse wave data points of the pulse waveform of FIG. 13 vary.

FIG. 14 is a graph showing how PP intervals measured at successive pulse wave data points of the pulse waveform 55 of FIG. 13 vary. If SW32 and SW35 are judged as noise and erased from the pulse wave data, PP interval values designated by the numerals 551 and 552 in FIG. 14 each represent the sum of two successive PP intervals in actuality. This kind of erratic variations in the PP interval could also be misinterpreted as indicating a symptom of arrhythmia of the subject as in the case of FIG. 12.

With the provision of the temporary erasure unit 443 and the noise filtration unit 444, however, the aforementioned problems (discussed with reference to FIGS. 11-14) can be avoided in the present embodiment. In the case of the pulse waveform 54 shown in FIG. 11, for example, the bottom peak values B22, B23 and the top peak values P22, P23 related respectively to the bottom-to-top amplitude values SW22 and SW23 are judged as data to be temporarily erased by the temporary erasure unit 443 and, thus, once transferred to the temporarily erased data storage unit 253.

The noise filtration unit 444 uses the fourth bottom-to-top amplitude value SW24 which has not been temporarily erased as a result of comparison with SW21 as the third peak-to-peak amplitude value AM3 (i.e., AM3=SW24), and judges whether a condition expressed by inequality SW24×(reference ratio "a")>SW23 (or SW23×(reference ratio "a") >SW24) is satisfied, where "a"=0.5. In the example of FIG. 11, the ratio between the third and fourth bottom-to-top amplitude values SW23, SW24 is larger than the reference ratio "a" (that is, one of the two values SW23, SW24 is not equal to or smaller than 50% of the other), so that the noise filtration unit 444 restores the bottom peak value B23 and the top peak value P23 related to the fourth bottom-to-top amplitude value SW23 by transferring the peak values B23, P23 from the temporarily erased data storage unit 253 back to the peak value storage unit 252. The noise filtration unit 444 also compares the second and fourth bottom-to-top amplitude values SW22, SW24 in a similar way. Since the ratio between the second and fourth bottom-to-top amplitude values SW22, SW24 is larger than the reference ratio "a", the noise filtration unit 444 restores the bottom peak value B22 and the top peak value P22 related to the fourth bottom-to-top amplitude value SW22 as well by transferring the peak values B22, P22 from the temporarily erased data storage unit 253 back to the peak value storage unit 252.

Consequently, the bottom peak values B22, B23 and the top peak values P22, P23 related respectively to the bottom-to-top amplitude values SW22 and SW23 representing true pulse waves are not erased but subjected to subsequent pulse wave data analysis. It is therefore possible to correctly determine intervals of the top peak values (bottom peak values). The provision of the temporary erasure unit 443 and the noise filtration unit 444 of the embodiment produces the same advantageous effect as discussed above with respect to the pulse waveform 55 shown in FIG. 13 as well.

When there exist a plurality of temporarily erased second peak-to-peak amplitude values (SW22, SW23), the noise filtration unit 444 successively compares SW22 and SW23 against the third peak-to-peak amplitude value AM3 which is fixed to SW24 (i.e., AM3=SW24) in the aforementioned example of the aforementioned comparison operation. As an alternative, the third peak-to-peak amplitude value AM3 used for comparison may be successively changed. For example, if it is determined to cancel classification of SW23 as temporarily erased data as a result of a comparison between SW23 and SW24, the third peak-to-peak amplitude value AM3 used for a comparison between SW23 and SW22 may be changed to SW23 (i.e., AM3=SW23).

Figure 5:
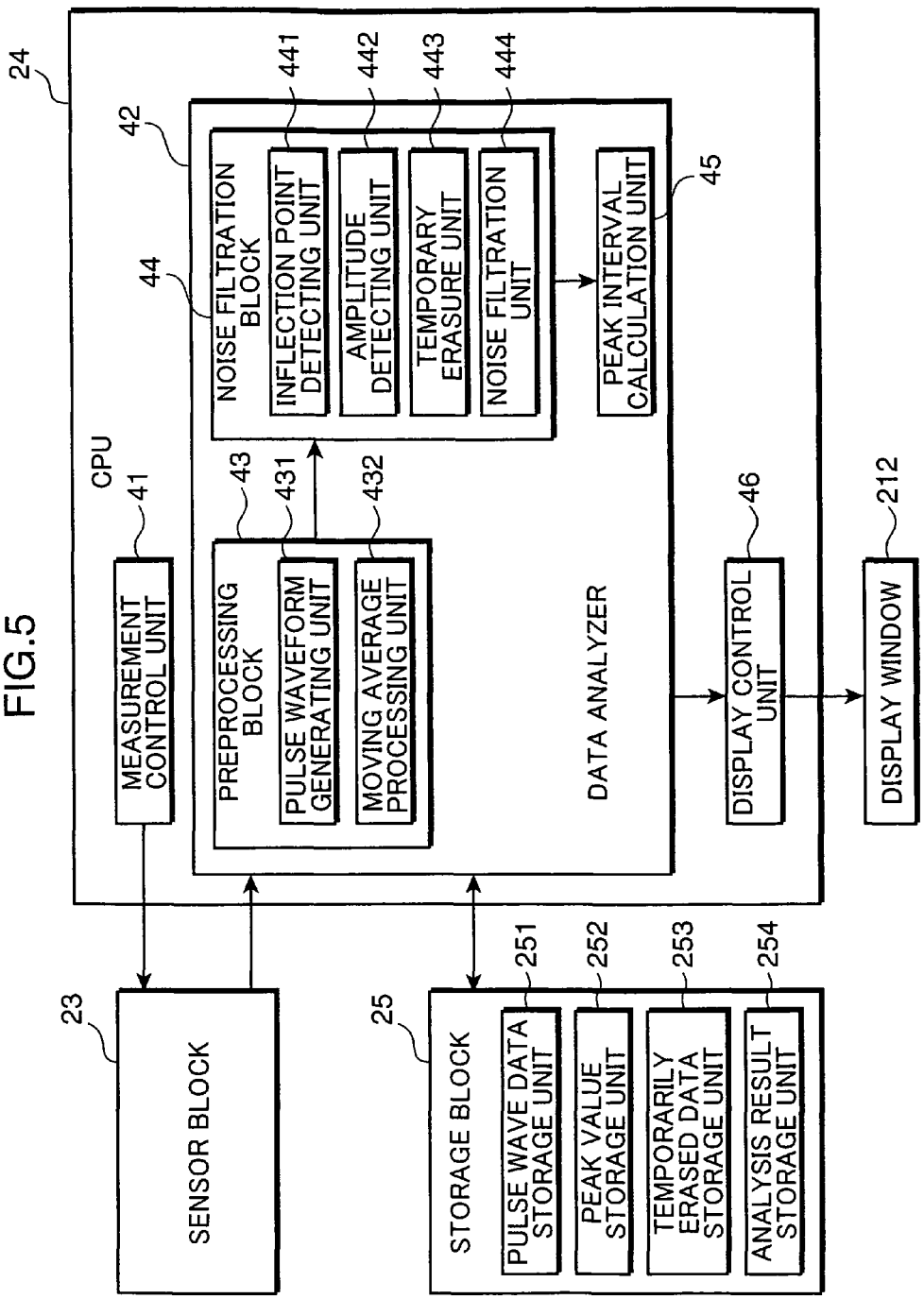
FIG. 5 is a functional block diagram of a central processing unit (CPU) of the pulse wave data analyzing system shown in FIG. 2.

Reverting to FIG. 5, the peak interval calculation unit 45 performs operation for calculating intervals of the top peak values (or bottom peak values) based on the pulse waveform from which noise components have been removed by the noise filtration unit 444. In the case of the pulse waveform 52 shown in FIG. 9, for example, the peak interval calculation unit 45 calculates the time interval X1 between the top peak values P1 and P3 from the time information stored in association with the top peak value P1 and the time information stored in association with the top peak value P3. Subsequently, the display control unit 46 calculates the time interval X2 between the top peak values P3 and P5, and so on in a similar way. Results of analysis of the pulse wave data thus obtained are stored in the analysis result storage unit 254 of the storage block 25.

Figure 15:
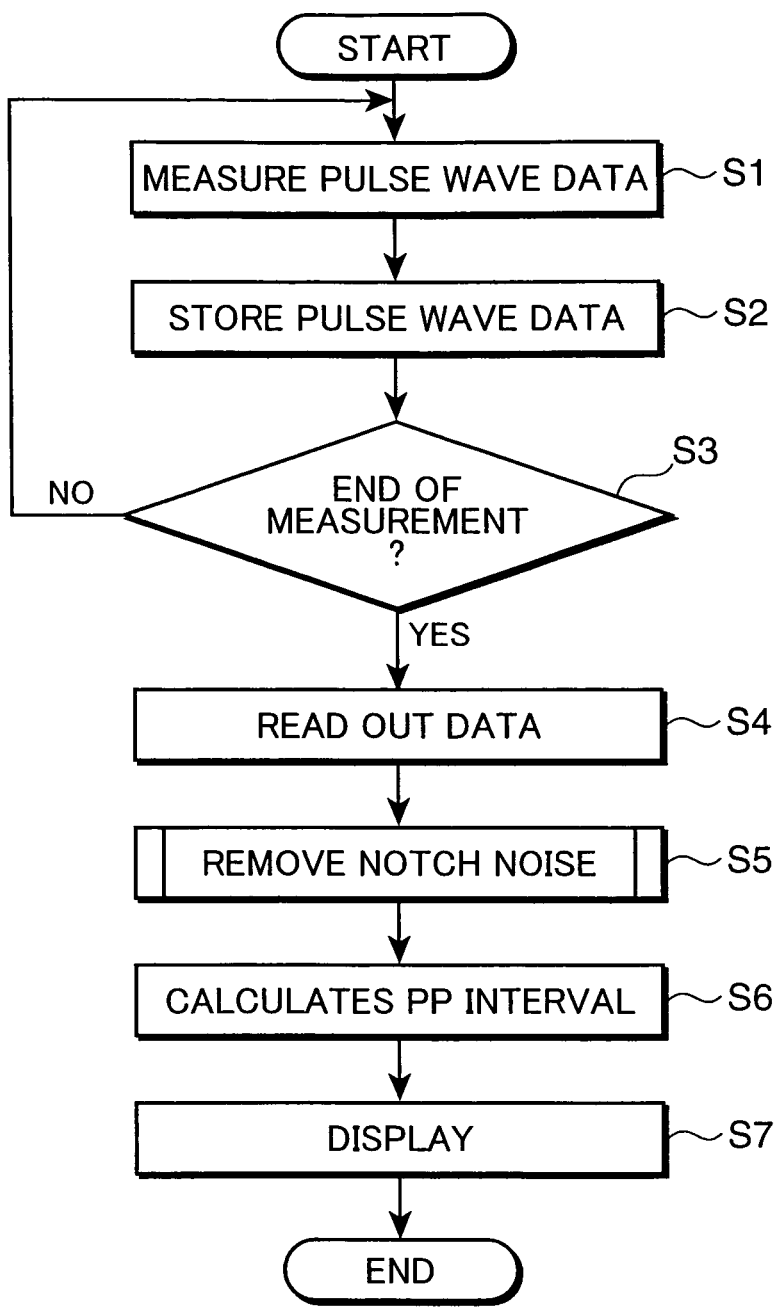
FIG. 15 is a flowchart showing an overall routine followed by a pulse wave measuring apparatus in calculating PP intervals.

The working of the pulse wave measuring apparatus 20 thus configured is now described hereinbelow. FIG. 15 is a flowchart showing an overall routine followed by the pulse wave measuring apparatus 20 in calculating PP intervals.

Shown in this flowchart is a procedure in which pulse wave data detected in a specified period of measurement time is once stored in the storage block 25 and the data analyzer 42 calculates PP intervals using the pulse wave data read out later.

After the pulse wave measuring apparatus 20 has been prepared to start measurement with the probe 22 mounted on a fingertip of the subject, the sensor block 23 detects pulse wave data at specified sampling intervals under the control of the measurement control unit 41 of the CPU 24 (step S1). Next, the measurement control unit 41 stores digital pulse wave data output from the A/D converter 234 in the pulse wave data storage unit 251 of the storage block 25 (step S2). The measurement control unit 41 then judges whether the pulse wave measuring apparatus 20 has performed measurement operation for the specified period of measurement time based on timer information, for instance (step S3). If the specified period of measurement time has not passed yet (No in step S3), the measurement control unit 41 causes the sensor block 23 to repeat steps S1 and S2 at a next sampling cycle.

If the specified period of measurement time has already passed (Yes in step S3), the data analyzer 42 reads out the pulse wave data stored in the pulse wave data storage unit 251 (step S4). Then, after the preprocessing block 43 has performed the particular preprocessing operation (e.g. moving average processing operation) on the raw pulse wave data, the noise filtration block 44 performs a notch noise filtering subroutine for removing notch noise components (step S5). Subsequently, the peak interval calculation unit 45 calculates PP intervals of pulse waves (step S6) and the display control unit 46 performs the data processing operation for properly formatting the results of pulse wave data analysis for on-screen presentation (step S7) to complete the routine of FIG. 15.

In a case where pulse wave measurement is performed by the pulse wave measuring apparatus 20' (first device) and data analysis by the personal computer 30 (second device), for example, the aforementioned operation of step S4 is performed through data communication between the first and second devices. Also, when the pulse wave data is analyzed on a real-time basis, the aforementioned operations of steps S4 to S6 are carried out in real time while the same is being measured, and the results of pulse wave data analysis are successively displayed on the display window 212.

Figure 16:
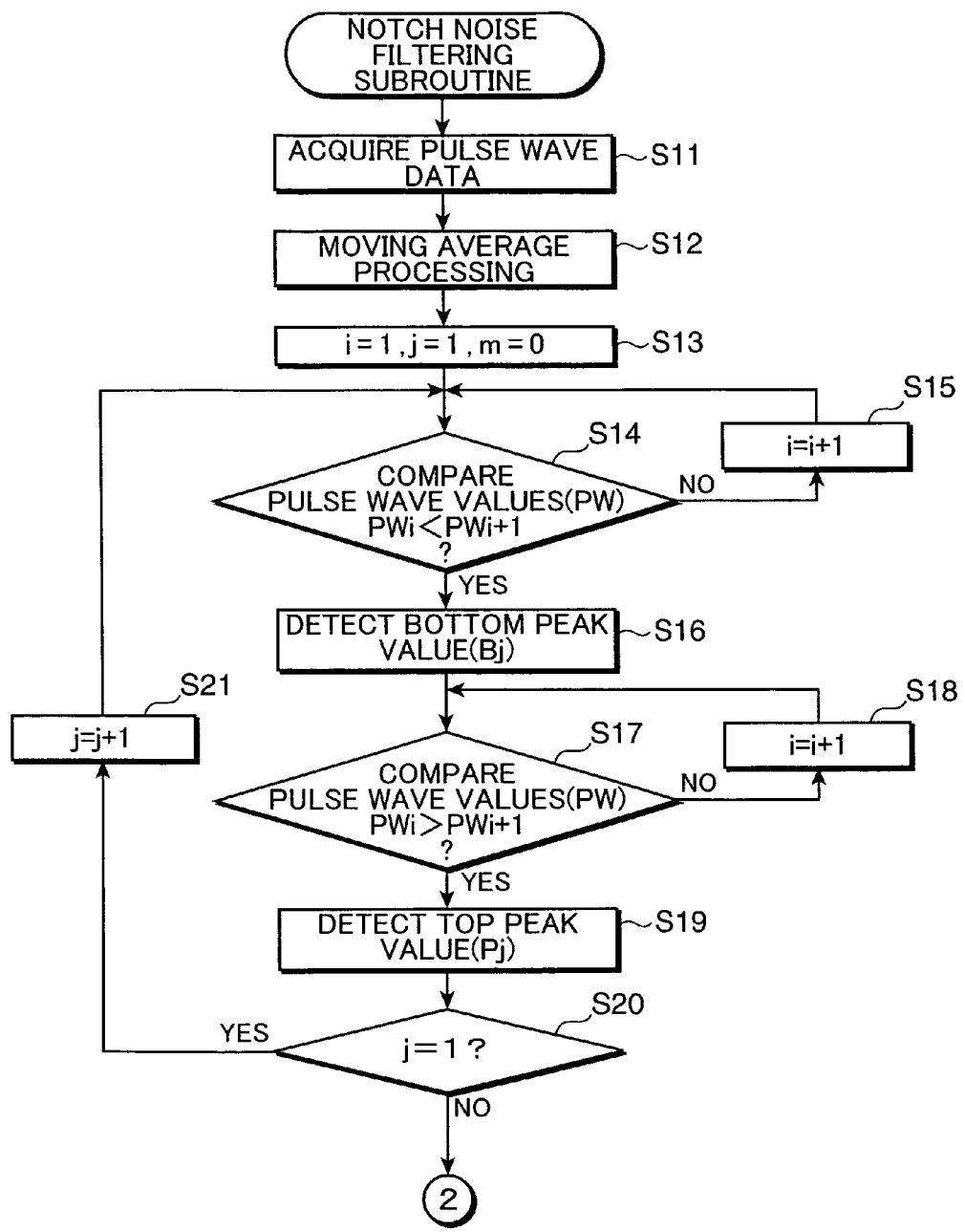
FIG. 16 is a first portion of a detailed flowchart showing a notch noise filtering subroutine according to the preferred embodiment.
Figure 17:
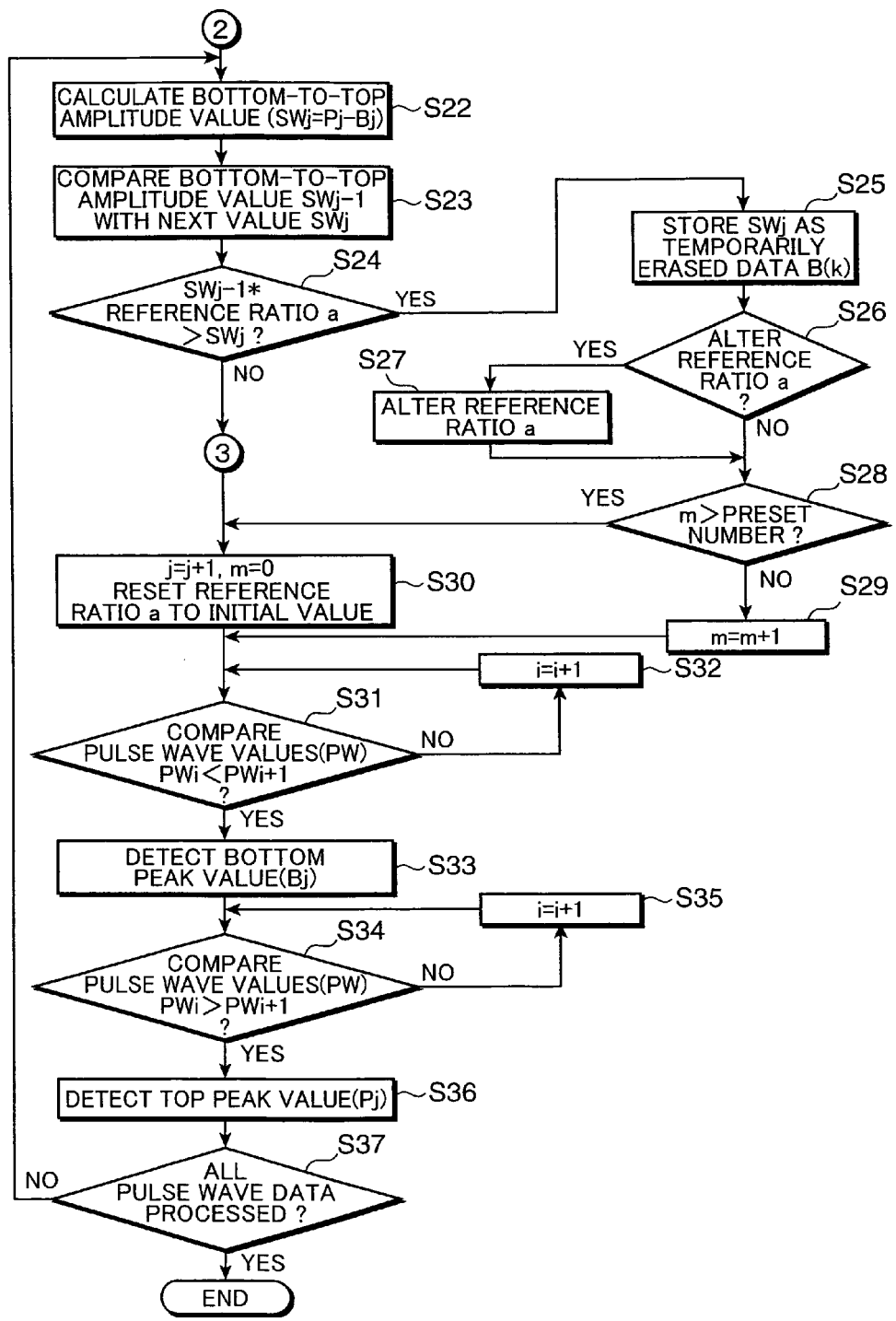
FIG. 17 is a second portion of the flowchart showing the notch noise filtering subroutine according to the preferred embodiment.
Figure 18:
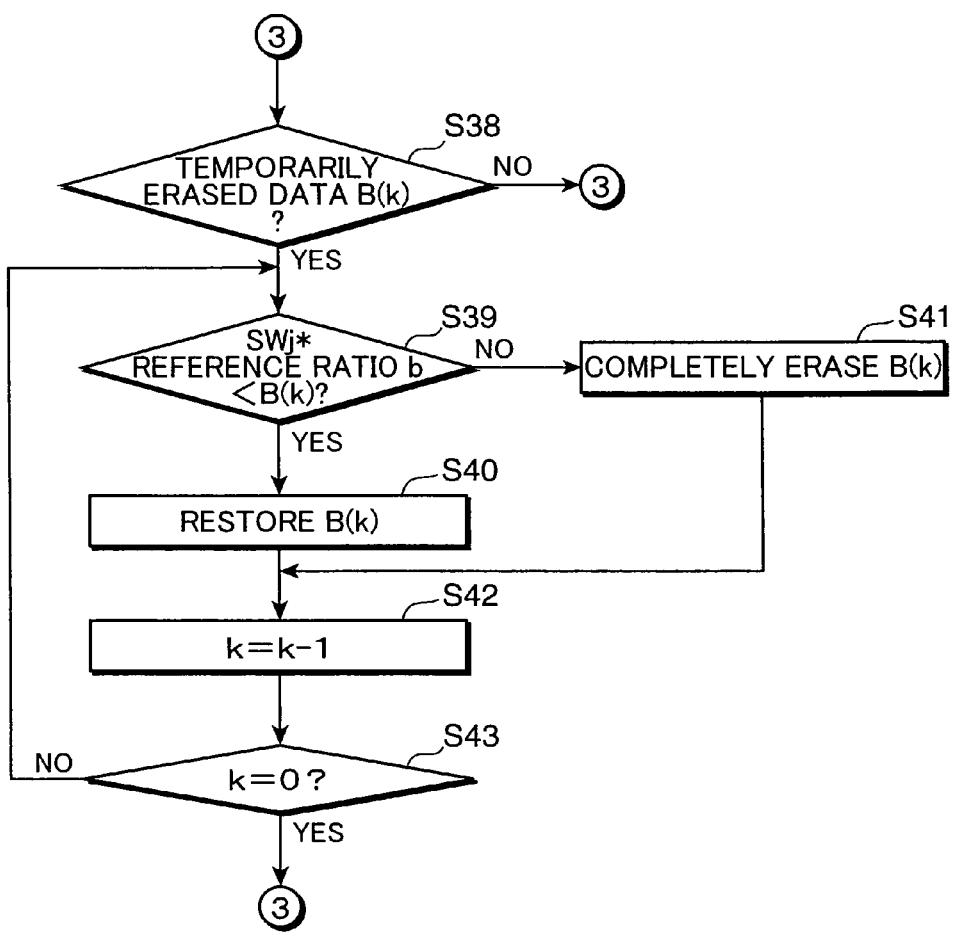
FIG. 18 is a third portion of the flowchart showing the notch noise filtering subroutine, or data restoration judgment operation, according to the preferred embodiment.
Figure 19:
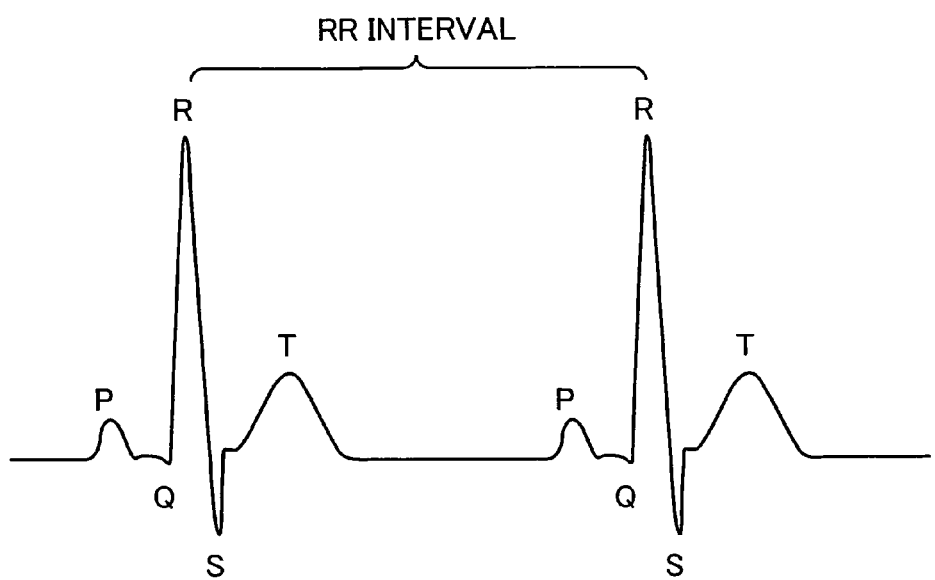
FIG. 19 is a diagram showing an RR interval read from a heartbeat waveform represented by an electrocardiogram.

FIGS. 16 to 18 are first to third portions of a detailed flowchart showing the aforementioned notch noise filtering subroutine of step S5. The following discussion illustrates an operating flow which is preferably applied to real-time pulse wave data analysis. The preprocessing block 43 sequentially reads out successive data values which are generated by the pulse waveform generating unit 431 and written in the pulse wave data storage unit 251 one after another with the progress of pulse wave measurement to acquire the pulse wave data (step S11). The moving average processing unit 432 performs the moving average processing operation on the pulse waveform generated by the pulse waveform generating unit 431 to smooth out the same (step S12). At this point, counter values i=1, j=1 and m=0 are set (step S13).

Then, the inflection point detecting unit 441 of the noise filtration block 44 judges whether a relationship expressed by (pulse wave value $PW_i$)<(pulse wave value $PW_{i+1}$) is satisfied (step S14). If the relationship of (pulse wave value $PW_i$)<(pulse wave value $PW_{i+1}$) is not satisfied (No in step S14), the counter value i is incremented by 1 (step S15) and step S14 is reexecuted. If the relationship of (pulse wave value $PW_i$)<(pulse wave value $PW_{i+1}$) is satisfied (Yes in step S14), on the contrary, the inflection point detecting unit 441 detects a current pulse wave value $PW_i$ as a bottom peak value $B_j$ (step S16).

Next, the inflection point detecting unit 441 judges whether a relationship expressed by (pulse wave value $PW_i$)>(pulse wave value $PW_{i+1}$) is satisfied (step S17). If the relationship of (pulse wave value $PW_i$)>(pulse wave value $PW_{i+1}$) is not satisfied (No in step S17), the counter value i is incremented by 1 (step S18) and step S17 is reexecuted. If the relationship of (pulse wave value $PW_i$)>(pulse wave value $PW_{i+1}$) is satisfied (Yes in step S17), on the contrary, the inflection point detecting unit 441 detects a current pulse wave value $PW_i$ as a top peak value $P_j$ (step S19). Then, the inflection point detecting unit 441 checks out whether j=1 (step S20). If j=1 (Yes in step S20), the counter value j is incremented by 1 (step S21) and, then, the inflection point detecting unit 441 returns to step S14 and reexecutes the above steps. If j≠1 (No in step S20), on the contrary, the data analyzer 42 proceeds to FIG. 17.

Subsequently, the amplitude detecting unit 442 performs mathematical operation for calculating a difference between the bottom peak value $B_j$ and the top peak value $P_j$ detected in succession along the time axis by the aforementioned steps of FIG. 16 to obtain a bottom-to-top amplitude value $SW_j$ (step S22). Then, the temporary erasure unit 443 performs operation for comparing $SW_j$ obtained in step S22 against a bottom-to-top amplitude value $SW_{j-1}$ which has been obtained one measurement cycle earlier by in the same way is a reference bottom-to-top amplitude value at the present point in time (step S23).

Now, the temporary erasure unit 443 judges whether a relationship expressed by $SW_{j-1}$*(reference ratio "a")>$SW_j$ is satisfied (step S24). If this relationship is satisfied (Yes in step S24), the temporary erasure unit 443 temporarily treats $SW_j$ as notch noise and transfers the bottom peak value $B_j$ and the top peak value $P_j$ related to the bottom-to-top amplitude value $SW_j$ to the temporarily erased data storage unit 253 as temporarily erased data $B_k$ (k=1, 2, 3, . . . ) (step S25).

If the aforementioned relationship is not satisfied (No in step S24), on the contrary, the currently obtained bottom-to-top amplitude value $SW_j$ is used as the reference bottom-to-top amplitude value for a bottom-to-top amplitude value obtained in a succeeding measurement cycle. The bottom-to-top amplitude value $SW_j$ is also used as a reference bottom-to-top amplitude value in subsequent data restoration judgment operation for judging whether to restore the temporarily erased data $B_k$ as will be later discussed with reference to FIG. 18. After the data restoration judgment operation, the counter value j is incremented by 1 (step S30) and, then, the inflection point detecting unit 441 performs operation for obtaining a bottom peak value $B_j$ and a top peak value $P_j$ in the succeeding measurement cycle (steps S31 to S36) in the same way as already discussed with reference to steps S14 to S19.

Following step S25, on the other hand, the temporary erasure unit 443 judges whether the reference ratio "a" should be altered (step S26) and, if the reference ratio "a" is to be altered, the temporary erasure unit 443 alters the reference ratio "a" (step S27). A purpose of altering the reference ratio "a" is to make it possible to neatly filter out low-level notch noise without erasing true pulse wave data while removing high-level notch noise. When the aforementioned comparison is repeatedly made by using one bottom-to-top amplitude value $SW_{j-1}$ as the reference bottom-to-top amplitude value, the temporary erasure unit 443 may performs the comparison operation using the reference ratio "a" of 0.5 ("a"=0.5) twice and then alter the reference ratio "a" to 0.1 ("a"=0.1) for succeeding comparisons as previously discussed. This is however one exemplary approach of the embodiment and the embodiment is not limited thereto.

The temporary erasure unit 443 judges whether the number m of repetitive comparisons made by using the same bottom-to-top amplitude value $SW_{j-1}$ as the reference bottom-to-top amplitude value has exceeded a preset number of times (e.g., 5 times) (step S28). If the preset number of times is exceeded (Yes in step S28), operation proceeds to step S30 in which the reference ratio "a" is reset to an initial value. If the preset number of times is not exceeded (No in step S28), the counter value m is incremented by 1 (step S29) operation proceeds to step S31.

FIG. 18 is a flowchart showing the data restoration judgment operation. In a case where the judgment result in step S24 is in the negative, a judgment is made as to whether any temporarily erased data $B_k$ exists in the temporarily erased data storage unit 253 (step S38). If no temporarily erased data $B_k$ exists (No in step S38), it is not necessary to make a data restoration judgment so that operation proceeds to step S30. If any temporarily erased data $B_k$ exists (Yes in step S38), the noise filtration unit 444 judges whether a relationship expressed by $SW_j^*$(reference ratio b)>$B_k$ is satisfied (step S39). If there exist a plurality of temporarily erased data, the value of k is determined to select data obtained at a point in time closest to a point in time when the bottom-to-top amplitude value $SW_j$ was obtained. The reference ratio b in the aforementioned inequality of step S39 is a threshold chosen as appropriate as a criterion used in determining whether to restore the temporarily erased data $B_k$. The reference ratio b may be set to a value equal to the initial value of the reference ratio "a" as mentioned above or a different value.

If the relationship of the aforementioned inequality is satisfied (Yes in step S39), the noise filtration unit 444 restores the temporarily erased data $B_k$ by transferring the same from the temporarily erased data storage unit 253 back to the peak value storage unit 252 (step S40). As a result, classification of the bottom peak value and the top peak value related to the temporarily erased data $B_k$ is canceled. If the relationship of the aforementioned inequality is not satisfied (No in step S39), on the contrary, the noise filtration unit 444 regards the temporarily erased data $B_k$ as notch noise and completely erases the bottom peak value and the top peak value related to the temporarily erased data $B_k$ from the temporarily erased data storage unit 253 (step S41).

Subsequently, a counter value k is decremented by 1 (step S42) and a judgment is made as to whether any temporarily erased data $B_k$ remains in the temporarily erased data storage unit 253 (step S43). If any temporarily erased data $B_k$ remains in the temporarily erased data storage unit 253 (No in step S43), operation returns to step S39 and the aforementioned data restoration judgment operation is performed on the next temporarily erased data $B_k$. If no more temporarily erased data $B_k$ remains in the temporarily erased data storage unit 253 (No in step S43), operation returns to step S30 of FIG. 17.

Returning to FIG. 17, a judgment is made as to whether processing of all the pulse wave data obtained by measurement has been completed (step S37). If the pulse wave data processing is incomplete (No in step S37), operation returns to step S22 and the aforementioned processing steps are reexecuted. Specifically, the temporary erasure unit 443 repeatedly performs a comparison of bottom-to-top amplitude values while successively updating the reference bottom-to-top amplitude value. If the pulse wave data processing has been completed (Yes in step S37), on the contrary, the aforementioned notch noise filtering subroutine is finished. Since the notch noise filtering subroutine is executed in real time in the aforementioned manner, it is possible to calculate PP intervals of pulse waves on a real-time basis.

While the invention has thus far been discussed with reference to the preferred embodiment thereof, the invention is not limited thereto but embraces various modifications and alternatives, some of which are described hereunder.

The foregoing discussion of the preferred embodiment has illustrated an example in which bottom peak and top peak values of the pulse wave data classified as data to be temporarily erased by the temporary erasure unit 443 are transferred to the temporarily erased data storage unit 253 in the meantime. Instead of using this approach, the bottom peak and top peak values classified as temporarily erased data may be assigned a particular flag (temporary erasure identifier). In this case, when particular bottom peak and top peak values are judged to be treated as temporarily erased data, the temporary erasure unit 443 assigns a flag to these bottom peak and top peak values stored in the peak value storage unit 252 and temporarily transfers the same to the temporarily erased data storage unit 253. The noise filtration unit 444 cancels the flag when classification of these bottom peak and top peak values as temporarily erased data is to be canceled, whereas the noise filtration unit 444 completely erases the bottom peak and top peak values assigned with the flag when the pertinent bottom peak and top peak values are judged to be representing notch noise components.

Another variation of the foregoing embodiment is to classify typical patterns of PP intervals according to different symptoms and store these PP interval patterns as identification indices in the storage block 25, for example. In this variation of the embodiment, the data analyzer 42 may include a symptom identification unit which causes the peak interval calculation unit 45 to compare measured PP intervals of pulse waves with the PP interval patterns and roughly estimate a symptom to which the measured PP intervals belong.

In the foregoing embodiment, the peak interval calculation unit 45 performs the operation for calculating the PP intervals of the top peak values (or bottom peak values) equivalent to RR intervals observed on an ECG based on the pulse waveform from which noise components have been removed. Instead of or in addition to this approach, the data analyzer 42 may employ an arrangement for determining bottom-to-top amplitude values of successive pairs of adjacent bottom peak and top peak values of the pulse waveform. For example, the amplitude detecting unit 442 may be controlled to determine the bottom-to-top amplitude value between the bottom peak value B1 and the top peak value P1, the bottom-to-top amplitude value between the bottom peak value B3 and the top peak value P3, the bottom-to-top amplitude value between the bottom peak value B5 and the top peak value P5, and so on, as diagnostic information from the pulse waveform 52 of FIG. 9 from which notch noise has been erased.

For example, an ECG taken from a with atrial fibrillation exhibits fluctuations in RR intervals and in bottom-to-top amplitude values as the pulse waveform taken from the same patient shows fluctuations in RR intervals and in bottom-to-top amplitude values. Therefore, it is possible to diagnose patients having atrial fibrillation by determining successive bottom-to-top amplitude values and evaluating fluctuations thereof.

When sympathetic nerves are stimulated, blood vessels contract, causing a reduction in bottom-to-top amplitude of the pulse waveform. Such a reduction in bottom-to-top amplitude of the pulse waveform compared to ordinary bottom-to-top amplitude, if detected, implies that the sympathetic nerves are normally working. It is therefore possible to diagnose autonomic disturbances based on a bottom-to-top amplitude measurement. Furthermore, it is possible to evaluate conditions of peripheral circulation using bottom-to-top amplitude values of the pulse waves.

It may possible to provide not only the aforementioned pulse wave data analyzing system S0 (S1, S2) and the pulse wave measuring apparatus 20 (20") but also a program for control such systems and apparatuses to carry out an intended pulse wave data analysis. Such a control program may be provided as a software product recorded on such a recording medium as a flexible disk, compact disc ROM (CD-ROM), ROM or RAM accompanying a computer. Alternatively, the control program may be provided as a software product downloadable through a network.

As described above, a pulse wave data analyzing method for extracting biometric information from pulse wave data taken from a living body comprises the steps of successively detecting bottom peak values and top peak values of the pulse wave data obtained by continuously measuring a pulse wave for a specific period of time along a time axis, combining two adjacent bottom and top peak values detected in succession along the time axis in pairs, calculating a bottom-to-top amplitude value which is a difference between the bottom and top peak values of each successive pair along the time axis, comparing a first peak-to-peak amplitude value and a second peak-to-peak amplitude value which correspond to two successive bottom-to-top amplitude values occurring in succession along the time axis, classifying the bottom and top peak values related to the second peak-to-peak amplitude value as temporarily erased data if the ratio of the second peak-to-peak amplitude value to the first peak-to-peak amplitude value is smaller than a preset threshold, comparing the second peak-to-peak amplitude value with a third peak-to-peak amplitude value which occurs in succession to the second peak-to-peak amplitude value, restoring the temporarily erased bottom and top peak values related to the second peak-to-peak amplitude value as data to be used for pulse wave data analysis by canceling classification of the bottom and top peak values related to the second peak-to-peak amplitude value as the temporarily erased data if the ratio between the second and third peak-to-peak amplitude values is larger than the preset threshold, and completely erasing the temporarily erased bottom and top peak values related to the second peak-to-peak amplitude value by regarding the bottom and top peak values as noise if the ratio between the second and third peak-to-peak amplitude values is not larger than the preset threshold.

According to this pulse wave data analyzing method, the bottom-to-top amplitude value is calculated from each successive pair of the two adjacent bottom and top peak values of the pulse wave data, the first peak-to-peak amplitude value and the second peak-to-peak amplitude value occurring in succession along the time axis are compared, and the bottom and top peak values related to the second peak-to-peak amplitude value are temporarily regarded as noise and classified as temporarily erased data if the ratio of the second peak-to-peak amplitude value to the first peak-to-peak amplitude value is smaller than a preset threshold. A bottom-to-top amplitude value caused by notch noise is usually so small (i.e., approximately equal to or smaller than typical bottom-to-top amplitude values of true pulse waves) that the bottom-to-top amplitude value representing notch noise does not exceed the typical bottom-to-top amplitude values. It is therefore possible to exactly determine intervals of top peaks (or bottom peaks) of the pulse wave data.

If the bottom and top peak values related to the second peak-to-peak amplitude value are regarded as notch noise and erased as a result of a comparison with the first peak-to-peak amplitude value alone, however, bottom and top peak values of true pulse waves may also be erased. For example, if a large first peak-to-peak amplitude value occurs due to a sudden bodily movement of a subject or respiratory variations in pulse wave amplitude, the bottom and top peak values related to the second peak-to-peak amplitude value may be erased even when this second peak-to-peak amplitude value is a bottom-to-top amplitude value of a true pulse wave. To avoid this inconvenience, the pulse wave data analyzing method employs an arrangement to classify the bottom and top peak values related to the second peak-to-peak amplitude value as temporarily erased data upon completion of a stage of the comparison with the first peak-to-peak amplitude value and decide whether to use the bottom and top peak values related to the second peak-to-peak amplitude value as data for pulse wave data analysis or to completely erase the bottom and top peak values related to the second peak-to-peak amplitude value by regarding these bottom and top peak values as notch noise. This arrangement makes it possible to exactly determine intervals of top peaks (or bottom peaks) of the pulse wave data even when the pulse wave data contains an erratically occurring bottom-to-top amplitude value.

Preferably, the pulse wave data analyzing method may further comprise the step of calculating one of a top peak interval and a bottom peak interval equivalent to an RR interval observed on an electrocardiogram from the pulse wave data from which the noise has been removed. According to this arrangement, the pulse wave data analyzing method can be used to properly diagnose cardiac arrhythmia, for instance, because the top peak interval or the bottom peak interval is determined from the pulse wave data from which the noise has been removed.

Preferably, the pulse wave data analyzing method may further comprise the step of calculating a bottom-to-top amplitude value from the pulse wave data from which the noise has been removed. According to this arrangement, the pulse wave data analyzing method can be used to conduct various kinds of diagnoses (e.g. diagnosis of activities of sympathetic nerves) by using bottom-to-top amplitude values obtained.

It may be preferable to further provide, after classifying the bottom and top peak values related to the second peak-to-peak amplitude value as the temporarily erased data, a step of adopting a bottom-to-top amplitude value calculated from bottom and top peak values detected in succession to the temporarily erased bottom and top peak values along the time axis as a new second peak-to-peak amplitude value and comparing the second peak-to-peak amplitude value with the first peak-to-peak amplitude value at least once, and adopting this bottom-to-top amplitude value as the third peak-to-peak amplitude value when a bottom-to-top amplitude value not satisfying a condition for classifying bottom and top peak values related thereto as temporarily erased data occurs, and comparing at least one second peak-to-peak amplitude value related to the temporarily erased data with the third peak-to-peak amplitude value.

This arrangement makes it possible to erase (temporarily erase) notch noise in a reliable fashion even when a plurality of notch noise components are detected between successively occurring bottom-to-top amplitude values of true pulse waves. On the other hand, when the first peak-to-peak amplitude value is derived from an erratically large bottom-to-top amplitude value, it is possible to prevent bottom and top peak values related to one or more second peak-to-peak amplitude values from being completely erased.

In this case, when there exist a plurality of second peak-to-peak amplitude values related to the temporarily erased data and classification of the bottom and top peak values related to one of the plural second peak-to-peak amplitude values is canceled as a result of a comparison with the third peak-to-peak amplitude value, the aforementioned one of the plural second peak-to-peak amplitude values is adopted as the third peak-to-peak amplitude value and another one of the plural second peak-to-peak amplitude values is compared with the third peak-to-peak amplitude value thus adopted. This arrangement makes it possible to evaluate goodness of the temporarily erased bottom and top peak values while successively changing the third peak-to-peak amplitude value used for comparison when there exist a plurality of second peak-to-peak amplitude values related to the temporarily erased data.

Further, the aforementioned threshold may be preferably altered at least once during execution of the aforementioned operation for comparing the second peak-to-peak amplitude value with the first peak-to-peak amplitude value at least once. This arrangement makes it possible to remove notch noise in a reliable fashion according to situations. For example, if the threshold of the ratio between the first and second (second and third) peak-to-peak amplitude values is decreased with an increase in the number of repetitive comparisons, it is possible to successively remove notch noise components producing relatively large to relatively small bottom-to-top amplitude values in a reliable fashion.

A pulse wave data analyzing system for extracting biometric information from pulse wave data taken from a living body comprises a pulse wave sensor for acquiring the pulse wave data varying along a time axis by measuring a pulse wave of a subject at specified sampling intervals, and a data analyzer for analyzing the pulse wave data. The data analyzer includes an inflection point detecting unit for successively detecting bottom and top peak values occurring along the time axis from the pulse wave data, an amplitude detecting unit for combining two adjacent bottom and top peak values occurring in succession along the time axis in pairs and calculating a bottom-to-top amplitude value which is a difference between the bottom and top peak values of each successive pair along the time axis, a temporary erasure unit for comparing a first peak-to-peak amplitude value and a second peak-to-peak amplitude value which correspond to two successive bottom-to-top amplitude values occurring in succession along the time axis and classifying the bottom and top peak values related to the second peak-to-peak amplitude value as temporarily erased data if the ratio of the second peak-to-peak amplitude value to the first peak-to-peak amplitude value is smaller than a preset threshold, a noise filtration unit for comparing the second peak-to-peak amplitude value with a third peak-to-peak amplitude value which occurs in succession to the second peak-to-peak amplitude value, restoring the temporarily erased bottom and top peak values related to the second peak-to-peak amplitude value by canceling classification of the bottom and top peak values related to the second peak-to-peak amplitude value as the temporarily erased data if the ratio between the second and third peak-to-peak amplitude values is larger than the preset threshold, and completely erasing the temporarily erased bottom and top peak values related to the second peak-to-peak amplitude value by regarding the bottom and top peak values as noise if the ratio between the second and third peak-to-peak amplitude values is not larger than the preset threshold.

According to this configuration, the inflection point detecting unit of the data analyzer detects bottom and top peak values from the pulse wave data acquired by the pulse wave sensor, and the amplitude detecting unit calculates a bottom-to-top amplitude value from each pair of two adjacent bottom and top peak values occurring in succession along the time axis. Then, the temporary erasure unit compares the first and the second peak-to-peak amplitude values occurring in succession along the time axis and classifies the bottom and top peak values related to the second peak-to-peak amplitude value as temporarily erased data by temporarily regarding these bottom and top peak values as noise if the ratio of the second peak-to-peak amplitude value to the first peak-to-peak amplitude value is smaller than the preset threshold. Subsequently, the noise filtration unit decides whether to use the bottom and top peak values related to the second peak-to-peak amplitude value as data for pulse wave data analysis or to completely erase the bottom and top peak values related to the second peak-to-peak amplitude value by regarding these bottom and top peak values as notch noise. Accordingly, the pulse wave data analyzing system thus configured can exactly determine intervals of top peaks (or bottom peaks) of the pulse wave data even when the pulse wave data contains a large peak-to-peak amplitude value caused by a sudden bodily movement of the subject or respiratory variations in pulse wave amplitude.

The pulse wave data analyzing system may be preferably further provided with a first storage unit for storing the bottom and top peak values detected by the inflection point detecting unit, and a second storage unit capable of storing data at least temporarily. The temporary erasure unit transfers the bottom and top peak values classified as the temporarily erased data from the first storage unit to the second storage unit when such bottom and top peak values occur, and the noise filtration unit transfers the bottom and top peak values once classified as the temporarily erased data from the second storage unit back to the first storage unit when canceling classification of the bottom and top peak values as the temporarily erased data. The pulse wave data analyzing system thus configured can easily perform the aforementioned operations for classifying the bottom and top peak values as temporarily erased data and canceling classification of the bottom and top peak values as the temporarily erased data by transferring the pertinent data between the first storage unit and the second storage unit.

The temporary erasure unit may preferably assign a temporary erasure identifier to the bottom and top peak values classified as the temporarily erased data when such bottom and top peak values occur, and the noise filtration unit removes the temporary erasure identifier from the bottom and top peak values classified as the temporarily erased data when canceling classification of the bottom and top peak values as the temporarily erased data and erases the bottom and top peak values assigned with the temporary erasure identifier when completely erasing these bottom and top peak values. The pulse wave data analyzing system thus configured can easily perform the aforementioned operations for classifying the bottom and top peak values as temporarily erased data and canceling classification of the bottom and top peak values as the temporarily erased data by assigning and removing the temporary erasure identifier.

The pulse wave data analyzing system may be preferably further provided with a display unit for displaying results of pulse wave data analysis obtained by the data analyzer, wherein the pulse wave sensor, the data analyzer and the display unit are built in a device which can be worn by the subject. The pulse wave data analyzing system can be configured as a wearable single-unit apparatus featuring superb portability and compactness, yet providing all necessary functions.

The pulse wave data analyzing system may be preferably further provided with a third storage unit for storing the pulse wave data acquired by the data analyzer, wherein the pulse wave data analyzing system is divided into a first device including the pulse wave sensor and the third storage unit, the first device being configured to be wearable by the subject, and a second device including the data analyzer, the second device being configured to have capability to take in the pulse wave data stored in the third storage unit by conducting data communication with the first device. Accordingly, the pulse wave data analyzing system can be configured as a combination of the first device for acquiring the pulse wave data and the second device (e.g., a personal computer) for conducting pulse wave data analysis, making it possible to conduct more sophisticated analyses.

The data analyzer may preferably analyse the pulse wave data in real time and displays pulse wave information obtained as a result of pulse wave data analysis on a display screen. The pulse wave data analyzing system thus configured permits a user to examine the pulse wave information on the display screen on a real-time basis, thereby providing enhanced convenience of operation.

The pulse wave data analyzing system may be preferably further provided with a fourth storage unit for storing the pulse wave information obtained by the data analyzer as a result of pulse wave data analysis. The pulse wave data analyzing system thus configured can store the pulse wave information obtained by pulse wave data analysis, making it possible to easily examine or statistically process the pulse wave information at a later time.

An analyzing program product for extracting biometric information from pulse wave data taken from a living body comprises a recording medium, and a pulse wave data analyzing program recorded on the recording medium. The pulse wave data analyzing program causes a data analyzer for analyzing the pulse wave data to read out the pulse wave data varying along a time axis acquired by measuring a pulse wave of a subject at specified sampling intervals, successively detect bottom peak values and top peak values of the pulse wave data, combine two adjacent bottom and top peak values detected in succession along the time axis in pairs, calculate a bottom-to-top amplitude value which is a difference between the bottom and top peak values of each successive pair along the time axis, compare a first peak-to-peak amplitude value and a second peak-to-peak amplitude value which correspond to two successive bottom-to-top amplitude values occurring in succession along the time axis, classify the bottom and top peak values related to the second peak-to-peak amplitude value as temporarily erased data if the ratio of the second peak-to-peak amplitude value to the first peak-to-peak amplitude value is smaller than a preset threshold, compare the second peak-to-peak amplitude value with a third peak-to-peak amplitude value which occurs in succession to the second peak-to-peak amplitude value, restore the temporarily erased bottom and top peak values related to the second peak-to-peak amplitude value as data to be used for pulse wave data analysis by canceling classification of the bottom and top peak values related to the second peak-to-peak amplitude value as the temporarily erased data if the ratio between the second and third peak-to-peak amplitude values is larger than the preset threshold, completely erase the temporarily erased bottom and top peak values related to the second peak-to-peak amplitude value by regarding the bottom and top peak values as noise if the ratio between the second and third peak-to-peak amplitude values is not larger than the preset threshold, and perform specific pulse wave analysis on the pulse wave data from which the noise has been removed.

According to the pulse wave data analyzing method, system and program, it is possible to remove noise components from the pulse wave data regardless of frequencies and waveform pattern of pulse waves. In particular, even when a pulse waveform obtained contains a large peak-to-peak amplitude value caused by a sudden bodily movement of the subject or respiratory variations in pulse wave amplitude, it is possible to remove only the noise components without erasing bottom and top peak values of true pulse waves. It is therefore possible to obtain exact pulse wave data by removing notch noise components contained therein, so that a medical worker can properly conduct various kinds of diagnoses based on such pulse wave data.

As the pulse wave data analyzing method, system and program make it possible to properly remove noise components contained in the pulse wave data and exactly detect peaks in the pulse waveform, the user can determine PP intervals of the pulse waves which are highly correlated with RR intervals observed on an ECG. Accordingly, the medical worker can diagnose cardiac arrhythmia with high accuracy and discover related diseases at an early time without forcing the subject to wear a stressful Holter monitor. The pulse wave data analyzing method and system are so user-friendly that these method and system can be easily applied even to aged persons. The pulse wave data analyzing method and system are useful for screening patients having such abnormalities as atrial fibrillation at an early time that frequently occur in aged persons. A further advantage is that the subject can continue to use the pulse wave data analyzing system with low stress for a long period of time which would be necessary for ascertaining effect of a medicinal treatment. In the case of a patient with atrial fibrillation who has been given medication, for example, it is necessary to confirm that atrial fibrillation does not occur for a period of approximately two weeks until complete recovery can be ascertained.

What is claimed is:

1. A pulse wave data analyzing method for extracting biometric information from pulse wave data taken from a living body, said pulse wave data analyzing method conducted by using a processor, the method comprising the steps of:

successively detecting bottom peak values and top peak values of the pulse wave data obtained by continuously measuring a pulse wave for a specific period of time along a time axis;

pairing a detected bottom peak value with a corresponding detected adjacent top peak value, respectively, in a successive manner along the time axis to generate a plurality of successive pairs;

calculating bottom-to-top amplitude difference values representing a difference between the bottom and top peak values of each successive pair along the time axis to define a first maximum difference value, a second maximum difference value, and a third maximum difference value, wherein the first, second, and third maximum differences values obtained from the corresponding successive pairs occur in succession along the time axis;

comparing the first maximum difference value and the second maximum difference value;

classifying the bottom and top peak values corresponding to the second maximum difference value as temporarily erasable data if a ratio of the first maximum difference value to the second maximum difference value is greater than a predetermined threshold;

comparing the second maximum difference value with the third maximum difference value;

restoring the temporarily erasable data as data to be used for pulse wave data analysis if a ratio between the second maximum difference value and the third maximum difference value is larger than the predetermined threshold; and completely erasing the temporarily erasable data as corresponding to noise if the ratio between the second maximum difference value and the third maximum difference value is not larger than the predetermined threshold.

2. The pulse wave data analyzing method according to claim 1 further comprising the step of calculating one of a top peak interval and a bottom peak interval equivalent to an RR interval observed on an electrocardiogram from the pulse wave data from which the noise has been removed.

3. The pulse wave data analyzing method according to claim 1 further comprising the step of calculating a bottom-to-top amplitude value from the pulse wave data from which the noise has been removed.

4. The pulse wave data analyzing method according to claim 1, further comprising, after classifying the bottom and top peak values related to the second peak-to-peak amplitude value as the temporarily erased data, the step of adopting a bottom-to-top amplitude value calculated from bottom and top peak values detected in succession to the temporarily erased bottom and top peak values along the time axis as a new second peak-to-peak amplitude value and comparing the second peak-to-peak amplitude value with the first peak-to-peak amplitude value at least once, and adopting this bottom-to-top amplitude value as the third peak-to-peak amplitude value when a bottom-to-top amplitude value not satisfying a condition for classifying bottom and top peak values related thereto as temporarily erased data occurs, and comparing at least one second peak-to-peak amplitude value related to the temporarily erased data with the third peak-to-peak amplitude value.

5. The pulse wave data analyzing method according to claim 4, wherein when there exist a plurality of second peak-to-peak amplitude values related to the temporarily erased data and classification of the bottom and top peak values related to one of the plural second peak-to-peak amplitude values is canceled as a result of a comparison with the third peak-to-peak amplitude value, said one of the plural second peak-to-peak amplitude values is adopted as the third peak-to-peak amplitude value and another one of the plural second peak-to-peak amplitude values is compared with the third peak-to-peak amplitude value thus adopted.

6. The pulse wave data analyzing method according to claim 4, wherein said threshold is altered at least once during execution of said operation for comparing the second peak-to-peak amplitude value with the first peak-to-peak amplitude value at least once.

7. An analyzing program product for extracting biometric information from pulse wave data taken from a living body, said analyzing program product comprising:
a non-transitory computer readable recording medium; and
a pulse wave data analyzing program recorded on non-transitory computer readable said recording medium, wherein said pulse wave data analyzing program causes a data analyzer for analyzing the pulse wave data to:
read out the pulse wave data varying along a time axis acquired by measuring a pulse wave of a subject at specified sampling intervals;
successively detect bottom peak values and top peak values of the pulse wave data; combine two adjacent bottom and top peak values detected in succession along the time axis in pairs;
calculate a bottom-to-top amplitude value which is a difference between the bottom and top peak values of each successive pair along the time axis;
compare a first peak-to-peak amplitude value and a second peak-to-peak amplitude value which correspond to two successive bottom-to-top amplitude values occurring in succession along the time axis;
classify the bottom and top peak values related to the second peak-to-peak amplitude value as temporarily erased data if the ratio of the second peak-to-peak amplitude value to the first peak-to-peak amplitude value is smaller than a preset threshold;
compare the second peak-to-peak amplitude value with a third peak-to-peak amplitude value which occurs in succession to the second peak-to-peak amplitude value;
restore the temporarily erased bottom and top peak values related to the second peak-to-peak amplitude value as data to be used for pulse wave data analysis by canceling classification of the bottom and top peak values related to the second peak-to-peak amplitude value as the temporarily erased data if the ratio between the second and third peak-to-peak amplitude values is larger than the preset threshold;
completely erase the temporarily erased bottom and top peak values related to the second peak-to-peak amplitude value by regarding the bottom and top peak values as noise if the ratio between the second and third peak-to-peak amplitude values is not larger than the preset threshold; and
perform specific pulse wave analysis on the pulse wave data from which the noise has been removed.

\* \* \* \* \*